US010759795B2

(12) United States Patent
Cushman et al.

(10) Patent No.: US 10,759,795 B2
(45) Date of Patent: Sep. 1, 2020

(54) AZA-A-RING INDENOISOQUINOLINE TOPOISOMERASE I POISONS

(71) Applicants: Purdue Research Foundation, West Lafayette, IN (US); National Institutes of Health, Bethesda, MD (US)

(72) Inventors: Mark S. Cushman, West Lafayette, IN (US); Daniel E. Beck, West Palm Beach, FL (US); Yves Pommier, Bethesda, MD (US)

(73) Assignees: PURDUE RESEARCH FOUNDATION, West Lafayette, IN (US); UNITED STATES DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 16/081,959

(22) PCT Filed: Mar. 15, 2017

(86) PCT No.: PCT/US2017/022389
§ 371 (c)(1),
(2) Date: Sep. 4, 2018

(87) PCT Pub. No.: WO2017/160898
PCT Pub. Date: Sep. 21, 2017

(65) Prior Publication Data
US 2019/0382401 A1 Dec. 19, 2019

Related U.S. Application Data

(60) Provisional application No. 62/308,392, filed on Mar. 15, 2016.

(51) Int. Cl.
*C07D 471/04* (2006.01)
*A61K 31/435* (2006.01)

(52) U.S. Cl.
CPC ................. *C07D 471/04* (2013.01)

(58) Field of Classification Search
None
See application file for complete search history.

(56) References Cited

U.S. PATENT DOCUMENTS

| | | | |
|---|---|---|---|
| 5,023,261 A | 6/1991 | Kamijo et al. | |
| 6,509,344 B1 | 1/2003 | Cushman et al. | |
| 6,828,319 B2 | 12/2004 | Jagtap et al. | |
| 7,312,228 B2 | 12/2007 | Cushman et al. | |
| 7,495,100 B2 | 2/2009 | Cushman et al. | |
| 7,781,445 B2 | 8/2010 | Cushman et al. | |
| 8,053,443 B2 | 11/2011 | Cushman et al. | |
| 8,686,146 B2 | 4/2014 | Cushman et al. | |
| 8,829,022 B2 | 9/2014 | Cushman et al. | |
| 8,912,213 B2 | 12/2014 | Cushman et al. | |
| 9,034,870 B2 | 5/2015 | Cushman et al. | |
| 9,073,920 B2 | 7/2015 | Cushman et al. | |
| 9,175,002 B2 | 11/2015 | Cushman et al. | |
| 9,206,193 B2 | 12/2015 | Cushman et al. | |
| 9,217,010 B2 | 12/2015 | Cushman et al. | |
| 9,328,073 B2 | 5/2016 | Cushman et al. | |
| 9,388,211 B2 | 7/2016 | Cushman et al. | |
| 9,399,660 B2 | 7/2016 | Cushman et al. | |
| 9,402,842 B2 | 8/2016 | Cushman et al. | |
| 9,682,990 B2 | 6/2017 | Cushman et al. | |
| 9,796,753 B2 | 10/2017 | Cushman et al. | |
| 2005/0010046 A1 | 1/2005 | LaVoie et al. | |
| 2006/0025595 A1* | 2/2006 | Cushman | C07D 217/26 546/21 |
| 2006/0247211 A1 | 11/2006 | Cushman et al. | |
| 2008/0090831 A1 | 4/2008 | LaVoie et al. | |
| 2008/0242692 A1 | 10/2008 | Cushman et al. | |
| 2008/0318995 A1 | 12/2008 | Cushman et al. | |
| 2012/0101119 A1 | 4/2012 | Cushman et al. | |
| 2012/0302563 A1 | 11/2012 | Cushman et al. | |
| 2013/0345252 A1 | 12/2013 | Cushman et al. | |
| 2014/0018360 A1 | 1/2014 | Cushman et al. | |
| 2014/0187547 A1 | 7/2014 | Cushman et al. | |
| 2014/0336188 A1 | 11/2014 | Cushman et al. | |
| 2015/0133445 A1 | 5/2015 | Cushman et al. | |
| 2015/0148370 A1 | 5/2015 | Cushman et al. | |
| 2015/0210686 A1 | 7/2015 | Dorsch et al. | |
| 2015/0218207 A1 | 8/2015 | Cushman et al. | |

(Continued)

FOREIGN PATENT DOCUMENTS

| WO | 0021537 A1 | 4/2000 |
|---|---|---|
| WO | 2004100891 A2 | 11/2004 |

(Continued)

OTHER PUBLICATIONS

Beck et al, Journal of Medicinal Chemistry, vol. 58, No. 9, pp. 3997-4015 (Year: 2015).*
Arpicco et al., Anticancer Prodrugs: An Overview of Major Strategies and Recent Developments, Current topics in medical chemistry, Jun. 2011, pp. 2345-2381.
Cinelli et al., Identification, Sythesis, and Biological Evaluation of Metabolites of the Experimental Cancer Treatment Drugs Indotecan (LMP400) and Indimitecan (LMP776) and Investigation of Isomerically Hydroxylated Indenoisoquinoline Analogues as Topoisomerase I Poisons, Journal of Medicinal Chemistry, 2012, pp. 10844-10862, American Chemical Society.
Staker et al., Structures of Three Classes of Anticancer Agents Bound to the Human Topoisomerase I—DNA Covalent Complex, Journal of Medicinal Chemistry, 2005, pp. 2336-2345, American Chemical Society.

(Continued)

*Primary Examiner* — Zinna Northington Davis
(74) *Attorney, Agent, or Firm* — Brannon Sowers & Cracraft PC

(57) ABSTRACT

The invention described herein pertains to four series of aza-A-ring indenoisoquinolines, which are inhibitors of topoisomerase IB (Top1), and the processes for preparing said aza-A-ring indenoisoquinolines. Also described are methods for treating cancer in mammals using the described aza-A-ring indenoisoquinoline compounds or pharmaceutical formulations thereof.

20 Claims, 4 Drawing Sheets

Specification includes a Sequence Listing.

(56) References Cited

U.S. PATENT DOCUMENTS

2015/0299246 A1 10/2015 Cushman et al.
2016/0081999 A1 3/2016 Cushman et al.
2016/0229888 A1 8/2016 Cushman et al.
2016/0318946 A1 11/2016 Cushman et al.

FOREIGN PATENT DOCUMENTS

| WO | 2005089294 A2 | 9/2005 |
| WO | 2007059008 A2 | 5/2007 |
| WO | 2008076767 A1 | 6/2008 |
| WO | 2009140467 A1 | 11/2009 |
| WO | 2011094416 A1 | 8/2011 |
| WO | 2012024437 A1 | 2/2012 |
| WO | 2012162513 A2 | 11/2012 |
| WO | 2015069766 A1 | 5/2015 |

OTHER PUBLICATIONS

Staker, Bart L. et al., The Mechanism of Topoisomerase I Poisoning by a Campthothecin Analog, Proc. Natl. Acad. Sci, 2002, pp. 15387-15392, vol. 99, No. 24.

Wall, Monroe E., et al., Bifunctional Reagents, Cross-linking of Pancreatic Ribonuclease With a Diimido Ester, J. Am. Chem. Soc., 1966, pp. 3888-3890, vol. 88, No. 16.

Paull, K D. et al., Display and Analysis of Patterns of Differential Activity of Drugs Against Human Tumor Cell Lines: Development of Mean Graph and COMPARE Algorithm, J. Natl. Cancer Inst., Jul. 19, 1989, pp. 1088-1091, vol. 81, No. 14.

Teicher, Beverly A., Next Generation Topoisomerase I Inhibitors: Rationale and Biomarker Strategies, Biochem. Pharmacology, 2008, pp. 1262-1271, vol. 75, Elsevier Inc.

Thomas, Craig J. et al., Camptothecin: Current Perspectives, Bioorganic & Medicinal Chemistry, 2004, pp. 1585-1604, vol. 12, Science Direct.

Pommier, Yves et al., DNA Topoisomerases and Their Poisoning by Anticancer and Antibacterial Drugs, Chemistry & Biology, May 28, 2010, pp. 421-433, vol. 17, Elsevier Ltd.

Stella, Valentino J., Prodrugs As Therapeutics, Expert Opinion on Therapeutic Patents, 2004, pp. 277-280, vol. 14, No. 3, Taylor & Francis.

Testa, Bernard, Prodrug Research: Futile or Fertile?, Biochemical Pharmacology, 2004, pp. 2097-2106, vol. 68, Science Direct.

Rautio, Jarkko et al., Prodrugs: Design and Clinical Applications, Nature Reviews Drug Discovery, Mar. 2008, pp. 255-270, vol. 7, Nature Publishing Group.

International Search Report, PCT/US17/16331, dated Apr. 28, 2017.

Jung "Prednisolone 21-sulfate sodium: a colon-specific pro-drug of prednisolone" 2003, 55, 1075-1082.

International Search Report, PCT/US2017/067206, dated Apr. 24, 2018.

International Search Report, PCT/US2017/022389, dated Jun. 9, 2017.

Kiselev et al. "Optimization of the Lactam Side Chain of 7-Azaindenoisoquinoline Topoisomerase I Inhibitors and Mechanism of Action Studies in Cancer Cells" Journal of Medicinal Chemistry. Feb. 6, 2014 (Feb. 6, 2014) vol. 57, p. 1289-1298; p. 1290.

Beck et al. 'Discovery of Potent Indenoisoquinoline Topoisomerase I Poisons Lacking the Nitro Toxicophore', Journal of medicinal chemistry, 2015, vol. 58.9, pp. 3997-4015. p. 3997, col. 1, para 2; p. 3998, col. 1, para 1; p. 4001, Scheme 8; p. 4003, Table 2.

Kiselev, Evgeny, et al. "7-azaindenoisoquinolines as topoisomerase I inhibitors and potential anticancer agents." Journal of medicinal chemistry 54.17 (2011): 6106-6116.

Kiselev, Evgeny, et al. "Azaindenoisoquinolines as topoisomerase I inhibitors and potential anticancer agents: a systematic study of structure-activity relationships." Journal of medicinal chemistry 55.4 (2012): 1682-1697.

Kiselev, Evgeny, et al. "Optimization of the lactam side chain of 7-azaindenoisoquinoline topoisomerase I inhibitors and mechanism of action studies in cancer cells." Journal of medicinal chemistry 57.4 (2014): 1289-1298.

Wang, Ping, et al. "Synthesis and biological evaluation of the first triple inhibitors of human topoisomerase 1, tyrosyl—DNA phosphodiesterase 1 (Tdp1), and tyrosyl—DNA phosphodiesterase 2 (Tdp2)." Journal of medicinal chemistry 60.8 (2017): 3275-3288.

Elsayed, Mohamed SA, et al. "Design and synthesis of chlorinated and fluorinated 7-azaindenoisoquinolines as potent cytotoxic anticancer agents that inhibit topoisomerase I" Journal of medicinal chemistry 60.13 (2017): 5364-5376.

Beck, Daniel E., et al. "Investigation of the Structure-Activity Relationships of Aza-A-Ring Indenoisoquinoline Topoisomerase I Poisons." Journal of medicinal chemistry 59.8 (2016): 3840-3853.

Beck Daniel E et al: "Synthesis and biological evaluation of new fluorinated and chlorinated indenoisoquinoline topoisomerase I poisons", Bioorganic & Medicinal Chemistry, vol. 24, No. 7, Feb. 9, 2016, pp. 1469-1479, XP029459043.

\* cited by examiner

AZA-A-RING INDENOISOQUINOLINE TOPOISOMERASE I POISONS

CROSS-REFERENCE TO RELATED APPLICATIONS

This application is a national stage entry under 35 U.S.C. § 371(b) of International Application No. PCT/US2017/022389, filed on Mar. 15, 2017, which claims priority under 35 U.S.C. § 119(e) to U.S. Provisional Patent Application Ser. No. 62/308,392, filed on Mar. 15, 2016, the contents of which are hereby incorporated by reference in their entirety into the present disclosure.

GOVERNMENT RIGHTS

This invention was made with government support CA089566 and CA023168 awarded by the National Institutes of Health. The government has certain rights in the invention.

TECHNICAL FIELD

The present disclosure generally relates to novel compounds as cancer therapeutics, and in particular to aza-A-ring indenoisoquinoline compounds as topoisomerase I poisons (inhibitors). The invention described herein also pertains to methods for treating cancer in mammals using aza-A-ring indenoisoquinolines.

STATEMENT OF SEQUENCE LISTING

A computer-readable form (CRF) of the Sequence Listing is submitted with this application. The file, generated on Jul. 9, 2019, is entitled 67410-03_ST25_txt. Applicant states that the content of the computer-readable form is the same and the information recorded in computer readable form is identical to the written sequence listing.

BACKGROUND

This section introduces aspects that may help facilitate a better understanding of the disclosure. Accordingly, these statements are to be read in this light and are not to be understood as admissions about what is or is not prior art.

DNA relaxation catalyzed by topoisomerase IB (Top1) is essential for replication and transcription in vertebrate cells. During this enzyme-mediated process, covalent Top1-DNA cleavage complexes are produced. Normally, cleavage complexes reverse rapidly and are undetectable in cells. However, DNA damage and certain cancer chemotherapeutic agents known as Top1 poisons can stabilize the cleavage complexes by preventing their reversal. As a result of the extended lifetimes of the cleavage complexes, advancing replication forks can collide with the DNA cleavage sites and produce DNA double-strand breaks. The DNA damage eventually causes the cell to enter apoptosis (Pommier, Y. DNA Topoisomerase I Inhibitors: Chemistry, Biology, and Interfacial Inhibition. *Chem. Rev.* 2009, 109, 2894-2902).

Several distinct Top poison chemotypes have been developed since the discovery of the natural product camptothecin (1, Scheme 1) and its unique mechanism of action (Oberlies, N. H., et al., *J. Nat. Prod.* 2004, 67, 129-135). Two derivatives of camptothecin are FDA-approved drugs used for the treatment of solid tumors, and several analogues are being investigated for the treatment of various cancers (Pommier, Y., et al., *Chem. Biol.* 2010, 17, 421-433). The potent anticancer activities of the members of this class are counterbalanced by problems with physicochemical properties, drug resistance, and patient tolerability. The shortcomings of the camptothecins include: (1) poor water solubility; (2) instability of the E-ring lactone at physiological pH, which hydrolyzes to a hydroxyacid that binds to plasma proteins; (3) rapid diffusion from their binding site in the Top1-DNA cleavage complexes, which may necessitate longer drug infusion times in order to maintain adequate concentrations of the ternary cleavage complexes; (4) dose-limiting toxicities including bone marrow suppression and severe dose-limiting diarrhea; (5) susceptibility to drug resistance by several Top1 point mutations; and (6) efficient removal from cancer cells by drug efflux pumps that results in drug resistance. There are still unmet clinical needs for better treatment options.

These limitations have resulted in the discovery of improved Top1 poisons. Two compounds, the indenoisoquinolines indotecan (LMP400, 2) and indimitecan (LMP776, 3), have been promoted to Phase I clinical trials at the National Cancer Institute (S. Kummar, et al., *Cancer Chemother Pharmacol* (2016) 78:73-81).

A third, structurally related indenoisoquinoline known as MJ-III-65 (LMP744, 4) has shown promising preclinical activity (Antony, S. et al., *Mol. Pharmacol.* 2005, 67, 523-530). The indenoisoquinolines overcome many of the drawbacks associated with the camptothecins (Pommier, Y. *Nat. Rev. Cancer* 2006, 6, 789-802).

Tyrosyl DNA phosphodiesterases 1 and 2 (TDP1 and TDP2) are DNA repair enzymes that process Top1- and Top2-mediated DNA lesions, respectively. TDP1 catalyzes the hydrolysis of the 3'-phosphotyrosyl-DNA linkages that result from degradation of Top1-DNA cleavage complexes. Bis(indenoisoquinoline) 5 displays potent Top1 inhibitory activity and its $IC_{50}$ values versus purified and whole cell extract-containing TDP1 are each approximately 1 µM. TDP2 catalyzes the hydrolysis of the 5'-phosphotyrosyl-DNA linkages that result from degradation of Top2-DNA cleavage complexes and it also displays weak activity against 3'-phosphotyrosyl-DNA linkages. There are currently no promising TDP2 inhibitor series. A series of deazaflavins (e.g. 6) with low nanomolar TDP2 inhibitory potencies was recently reported. However, the authors remarked that the chemical series is marred by poor cellular permeability. TDP1 and TDP2 can serve as mutual backups for the repair of stalled Top1-DNA cleavage complexes, which would make dual TDP1 and TDP2 inhibition a significant advancement.

Scheme 1. Known Topoisomerase Poisons

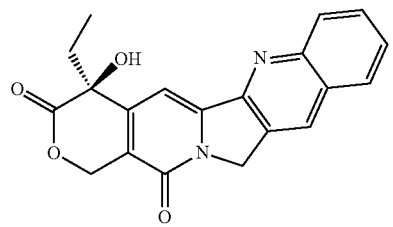

-continued

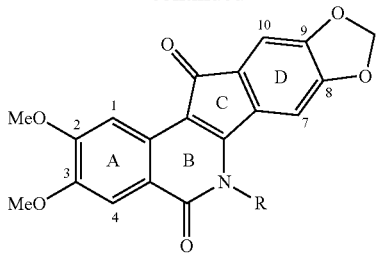

1

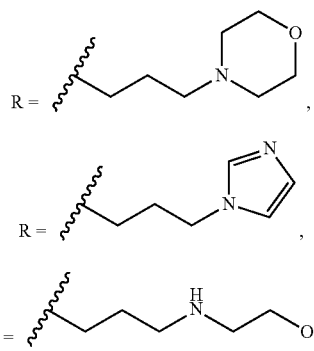

2

3

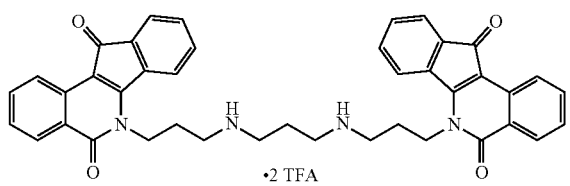

4

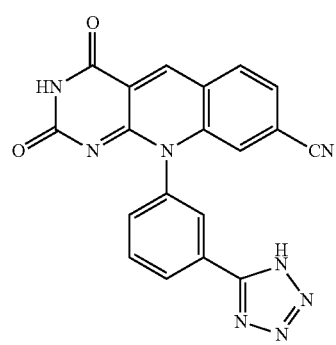

5

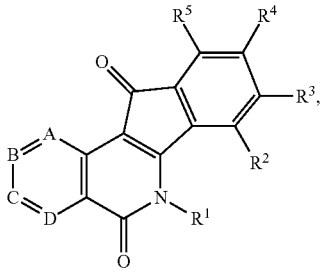

6

BRIEF SUMMARY OF INVENTION

In some illustrative embodiments, the invention is related to a compound of formula (I)

(I)

or a pharmaceutically acceptable salt, hydrate, prodrug, polymorph, or solvate thereof, wherein $R^1$ is an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted;

$R^2$, $R^3$, $R^4$ and $R^5$ represent four substituents each independently selected from the group consisting of hydrogen, halo, azido, cyano, nitro, hydroxy, amino, thio, and derivatives thereof; or any two adjacent substituents that are taken together with the attached carbons to form an optionally substituted heterocycle, and each of other two substituents is defined as above;

A is N or CH;
B is N or CH;
C is N or CH; and
D is N or CH.

In some preferred embodiments, the invention is related to a compound of formula (I), wherein $R^1$ is a $C_1$-$C_{12}$ alkyl, alkenyl, heteroalkyl, heteroalkenyl, or heterocyclyl.

In some preferred embodiments, the invention is related to a compound of formula (I), wherein $R^1$ is —$(CH_2)_n$R wherein n is 2, 3 or 4 and R is 1-imidazolyl, one of A, B, C, and D is N, and $R^2$, $R^3$, $R^4$ and $R^5$ are hydrogen.

In some preferred embodiments, the invention is related to a compound of formula (I), wherein $R^1$ is —$(CH_2)_n$R wherein n is 2, 3 or 4 and R is 1,2,4-triazol-2-yl, one of A, B, C, and D is N, and $R^2$, $R^3$, $R^4$ and $R^5$ are hydrogen.

In some preferred embodiments, the invention is related to a compound of formula (I), wherein $R^1$ is —$(CH_2)_n$R wherein n is 2, 3 or 4 and R is 1-morpholinyl, one of A, B, C, and D is N, and $R^2$, $R^3$, $R^4$ and $R^5$ are hydrogen.

In some preferred embodiments, the invention is related to a compound of formula (I), wherein $R^1$ is —$(CH_2)_n$R wherein n is 2, 3 or 4 and R is —$N(CH_3)_2$, one of A, B, C, and D is N, and $R^2$, $R^3$, $R^4$ and $R^5$ are hydrogen.

In some preferred embodiments, the invention is related to a compound of formula (I), wherein $R^1$ is —$(CH_2)_n$R wherein n is 2, 3 or 4 and R is amino, one of A, B, C, and D is N, and $R^2$, $R^3$, $R^4$ and $R^5$ are hydrogen.

In some preferred embodiments, the invention is related to a compound of formula (I), wherein $R^1$ is —$(CH_2)_n$R wherein n is 2, 3 or 4 and R is —$CH_2CH(OH)CH_2OH$, one of A, B, C, and D is N, and $R^2$, $R^3$, $R^4$ and $R^5$ are hydrogen.

In some preferred embodiments, the invention is related to a compound of formula (I), wherein A is N and B, C, and D are CH, and $R^2$, $R^3$, $R^4$ and $R^5$ are hydrogen.

In some preferred embodiments, the invention is related to a compound of formula (I), wherein B is N and A, C, and D are CH, and $R^2$, $R^3$, $R^4$ and $R^5$ are hydrogen.

In some preferred embodiments, the invention is related to a compound of formula (I), wherein C is N and A, B, and D are CH, and $R^2$, $R^3$, $R^4$ and $R^5$ are hydrogen.

In some preferred embodiments, the invention is related to a compound of formula (I), wherein D is N, A, B, and C are CH, and $R^2$, $R^3$, $R^4$ and $R^5$ are hydrogen.

In some preferred embodiments, the invention is related to a compound of formula (I), wherein one of A, B, C, and D is N, and $R^2$, $R^3$, $R^4$ and $R^5$ are hydrogen.

In some preferred embodiments, the invention is related to a compound of formula (I), wherein one of A, B, C, and D is N, $R^2$ and $R^5$ are hydrogen, and $R^3$ and $R^4$ are methoxy or together with the attached carbons form a five-membered heterocycle.

In some preferred embodiments, the compound of this invention is selected from the group consisting of

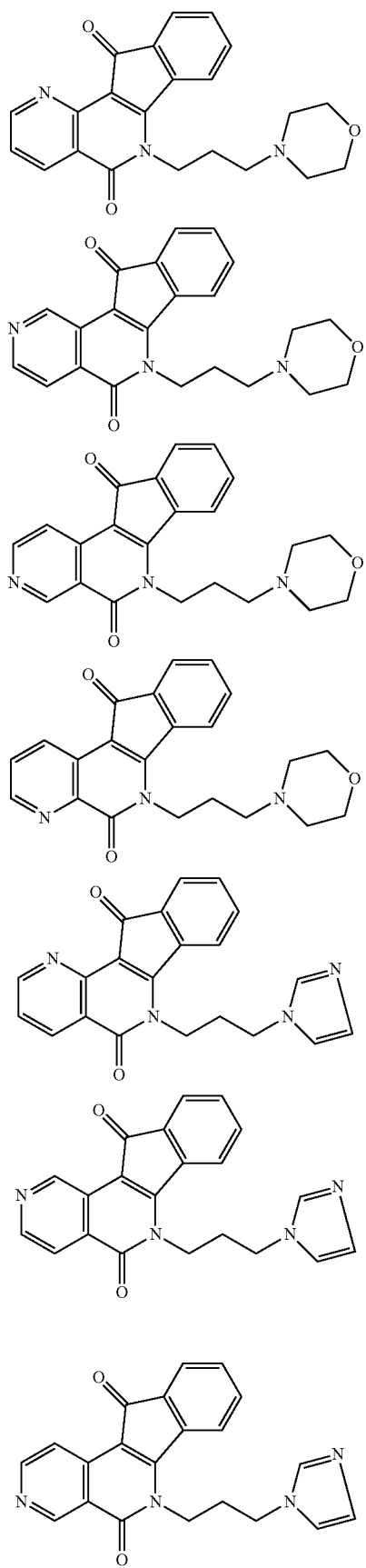
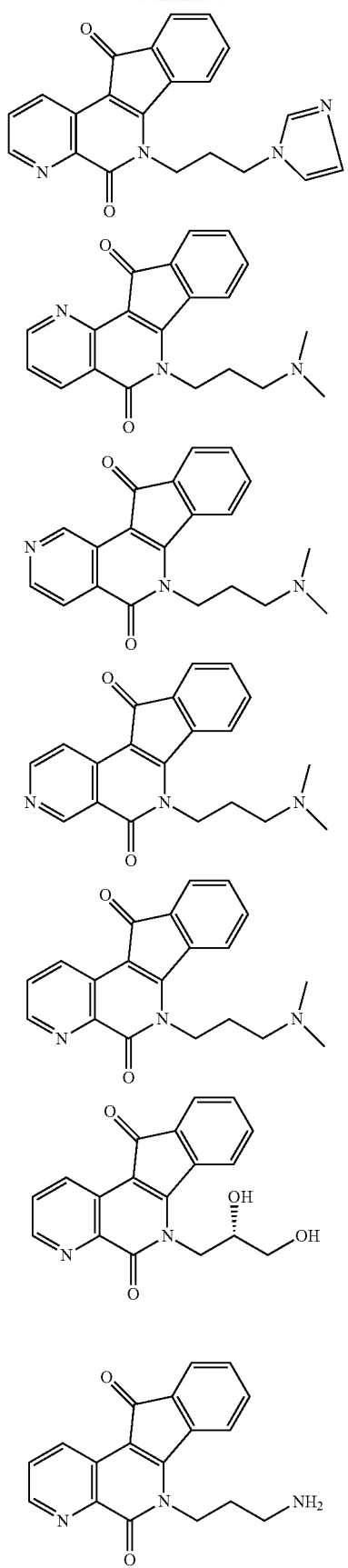

-continued

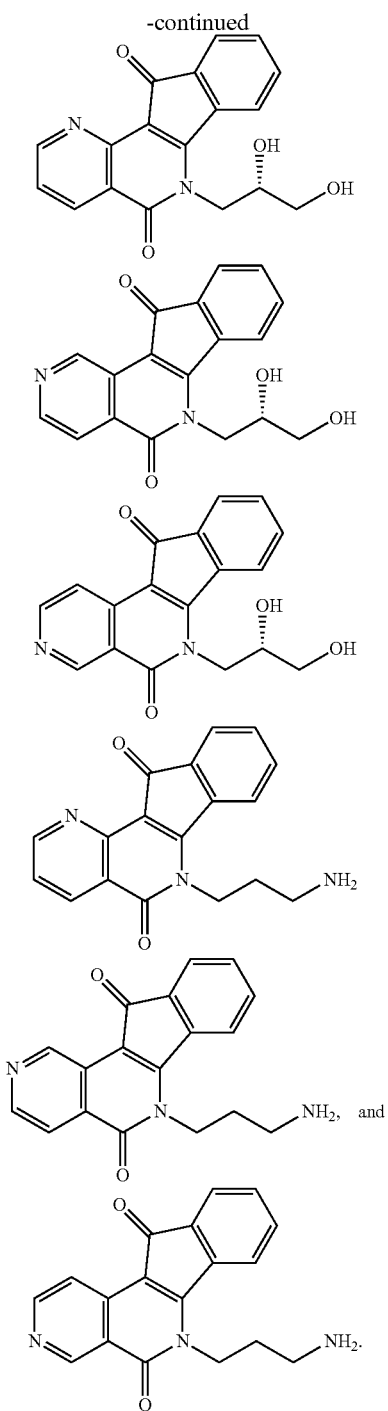

It is to be understood that all possible combinations of the various genera and subgenera of each of A, B, C, D, $R^1$, $R^2$, $R^3$, $R^4$ and $R^5$ described herein represent additional illustrative embodiments of compounds of the invention described herein. It is also to be understood that each of those additional illustrative embodiments of compounds may be used in any of the compositions, methods, and/or uses described herein.

In some embodiments, the invention is related to a pharmaceutical composition comprising one or more compounds disclosed herein, or a pharmaceutically acceptable salt thereof, together with one or more diluents, excipients or carriers.

In some embodiments, the invention is related to a pharmaceutical composition comprising one or more compounds disclosed herein, or a pharmaceutically acceptable salt thereof, together with one or more diluents, excipients or carriers, for use as a medicament.

In some embodiments, the invention is related to a pharmaceutical composition comprising one or more compounds disclosed herein, or a pharmaceutically acceptable salt thereof, together with one or more diluents, excipients or carriers, for use as a treatment for a cancer.

In some embodiments, the invention is related to a method for treating cancer comprising the step of administering a therapeutically effective amount of one or more compounds disclosed in any of the embodiments, and one or more carriers, diluents, or excipients, to a patient in need of relief from said cancer.

In some embodiments, the invention is related to a method for treating cancer comprising the step of administering a therapeutically effective amount of one or more compounds disclosed in any of the embodiments in combination with one or more other compounds of the same or different mode of action, and one or more carriers, diluents, or excipients, to a patient in need of relief from said cancer.

In another embodiment, pharmaceutical compositions containing one or more of the compounds are also described herein. In one aspect, the compositions include a therapeutically effective amount of the one or more compounds for treating a patient with cancer. It is to be understood that the compositions may include other component and/or ingredients, including, but not limited to, other therapeutically active compounds with the same or different modes of action, and one or more carriers, diluents, excipients, and the like. In another embodiment, methods for using the compounds and pharmaceutical compositions for treating patients with cancer are also described herein. In one aspect, the methods include the step of administering one or more of the compounds and/or compositions described herein to a patient with cancer. In another aspect, the methods include administering a therapeutically effective amount of the one or more compounds and/or compositions described herein for treating patients with cancer.

It is appreciated herein that the compounds described herein may be used alone or in combination with other compounds that may be therapeutically effective by the same or different modes of action. In addition, it is appreciated herein that the compounds described herein may be used in combination with other compounds that are administered to treat other symptoms of cancer, such as compounds administered to relieve pain, nausea, vomiting, and the like.

DETAILED DESCRIPTION

Figure 1A:
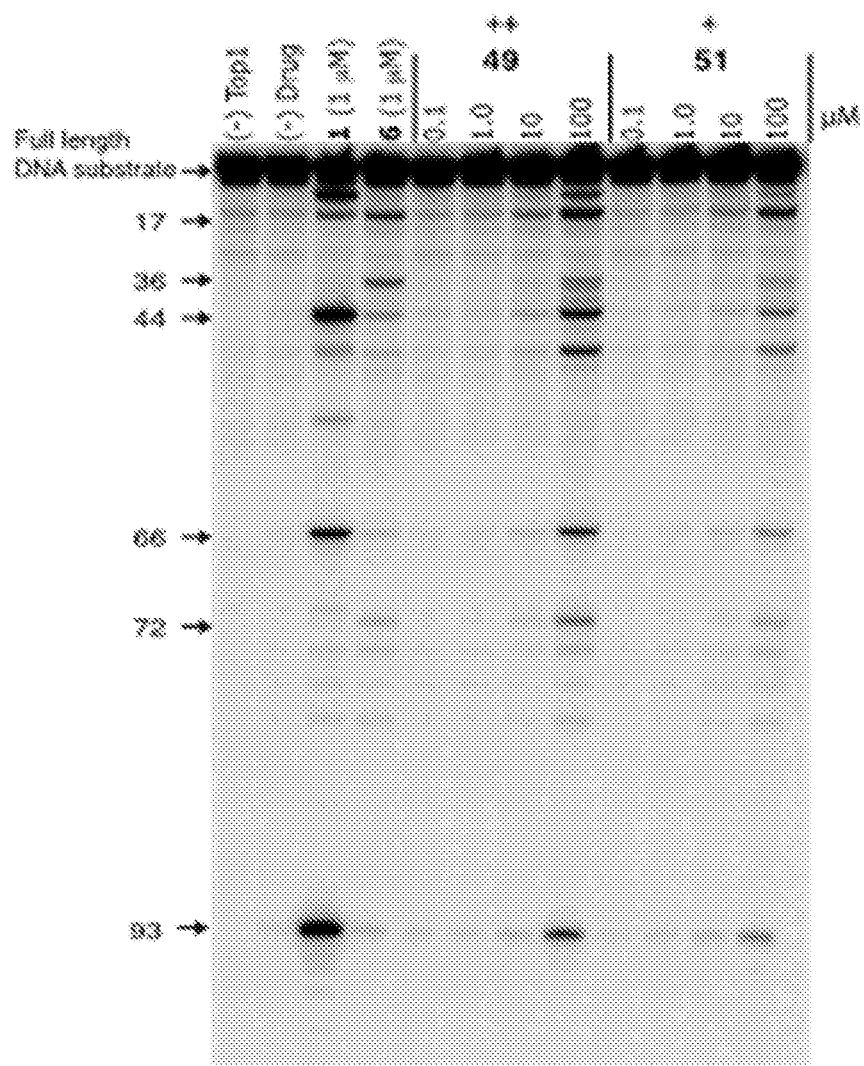
FIG. 1A is a gel showing the results of Top1-mediated DNA cleavage assay of concentration-response for 49 and 51. The numbers and arrows at the left indicate cleavage site positions. Gel-based assays include positive controls (i.e., 1 and 6). The combined intensities of the bands observed at different drug concentrations in the DNA cleavage electrophoresis gels are used to estimate the abilities of the topoisomerase I poisons to stabilize the cleavage complexes through inhibition of the religation reaction at several different DNA cleavage sites. The "+"-based scoring system is based on the activity of 1 µM camptothecin (1): 0, no activity; +, between 20 and 50% activity; ++, between 50 and 75% activity at the most effective drug concentration.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present invention provides four series of novel aza-A-ring indenoisoquinoline compounds as compounds as topoisomerase I (Top1) poisons (inhibitors). The invention described herein also pertains to methods for treating cancer in mammals using aza-A-ring indenoisoquinolines.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH=CH—, —CH=CHCH$_2$—, and the like. Examples of branched alkenyl groups include, but are not limited to, —CH=C(CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —CF(CH$_3$)$_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder, activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

In some illustrative embodiments, the invention is related to a compound of formula (I)

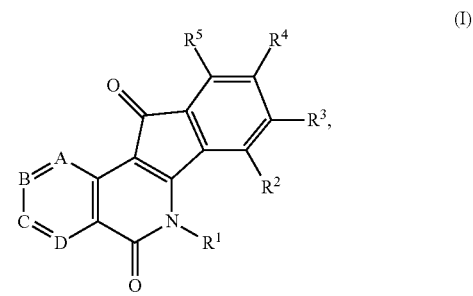

or a pharmaceutically acceptable salt, hydrate, prodrug, polymorph, or solvate thereof, wherein $R^1$ is an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted;

$R^2$, $R^3$, $R^4$ and $R^5$ represent four substituents each independently selected from the group consisting of hydrogen, halo, azido, cyano, nitro, hydroxy, amino, thio, and derivatives thereof; or any two adjacent substituents that are taken together with the attached carbons to form an optionally substituted heterocycle, and each of other two substituents is defined as above;

A is N or CH;

B is N or CH;

C is N or CH; and

D is N or CH.

In some preferred embodiments, the invention is related to a compound of formula (I), wherein $R^1$ is a $C_1$-$C_{12}$ alkyl, alkenyl, heteroalkyl, heteroalkenyl, or heterocyclyl.

In some preferred embodiments, the invention is related to a compound of formula (I), wherein $R^1$ is —$(CH_2)_n$R wherein n is 2, 3 or 4 and R is 1-imidazolyl, one of A, B, C, and D is N, and $R^2$, $R^3$, $R^4$ and $R^5$ are hydrogen.

In some preferred embodiments, the invention is related to a compound of formula (I), wherein $R^1$ is —$(CH_2)_nR$ wherein n is 2, 3 or 4 and R is 1,2,4-triazol-2-yl, one of A, B, C, and D is N, and $R^2$, $R^3$, $R^4$ and $R^5$ are hydrogen.

In some preferred embodiments, the invention is related to a compound of formula (I), wherein $R^1$ is —$(CH_2)_nR$ wherein n is 2, 3 or 4 and R is 1-morpholinyl, one of A, B, C, and D is N, and $R^2$, $R^3$, $R^4$ and $R^5$ are hydrogen.

In some preferred embodiments, the invention is related to a compound of formula (I), wherein $R^1$ is —$(CH_2)_nR$ wherein n is 2, 3 or 4 and R is —$N(CH_3)_2$, one of A, B, C, and D is N, and $R^2$, $R^3$, $R^4$ and $R^5$ are hydrogen.

In some preferred embodiments, the invention is related to a compound of formula (I), wherein $R^1$ is —$(CH_2)_nR$ wherein n is 2, 3 or 4 and R is amino, one of A, B, C, and D is N, and $R^2$, $R^3$, $R^4$ and $R^5$ are hydrogen.

In some preferred embodiments, the invention is related to a compound of formula (I), wherein $R^1$ is —$(CH_2)_nR$ wherein n is 2, 3 or 4 and R is —$CH_2CH(OH)CH_2OH$, one of A, B, C, and D is N, and $R^2$, $R^3$, $R^4$ and $R^5$ are hydrogen.

In some preferred embodiments, the invention is related to a compound of formula (I), wherein A is N and B, C, and D are CH, and $R^2$, $R^3$, $R^4$ and $R^5$ are hydrogen.

In some preferred embodiments, the invention is related to a compound of formula (I), wherein B is N and A, C, and D are CH, and $R^2$, $R^3$, $R^4$ and $R^5$ are hydrogen.

In some preferred embodiments, the invention is related to a compound of formula (I), wherein C is N and A, B, and D are CH, and $R^2$, $R^3$, $R^4$ and $R^5$ are hydrogen.

In some preferred embodiments, the invention is related to a compound of formula (I), wherein D is N, A, B, and C are CH, and $R^2$, $R^3$, $R^4$ and $R^5$ are hydrogen.

In some preferred embodiments, the invention is related to a compound of formula (I), wherein one of A, B, C, and D is N, and $R^2$, $R^3$, $R^4$ and $R^5$ are hydrogen.

In some preferred embodiments, the invention is related to a compound of formula (I), wherein one of A, B, C, and D is N, $R^2$ and $R^5$ are hydrogen, and $R^3$ and $R^4$ are methoxy or together with the attached carbons form a five-membered heterocycle. This class of compounds may be prepared using the procedures disclosed in this invention in combination with an analogous synthetic procedure previously reported by Lv, P. C. et al. (*J. Med. Chem.* 2016, 59(10):4890-4899).

In some preferred embodiments, the compound of this invention is selected from the group consisting of

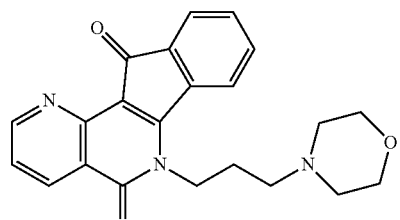

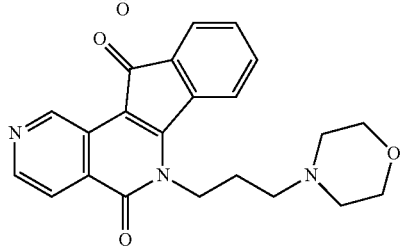

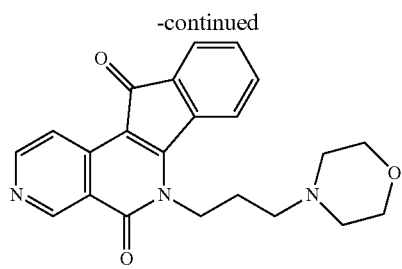

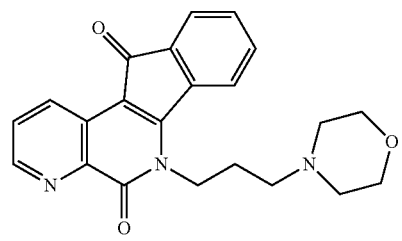

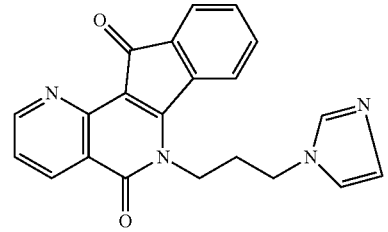

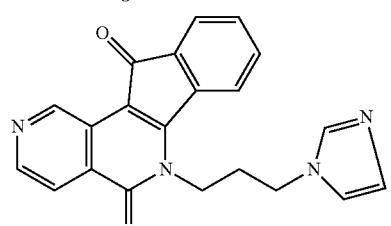

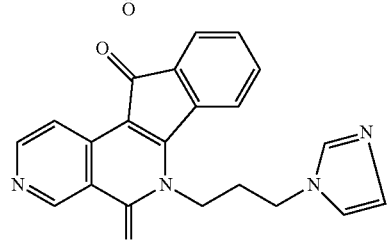

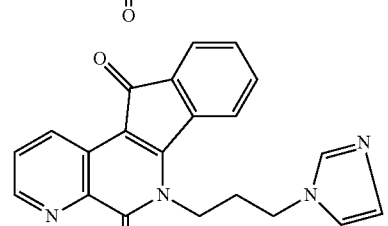

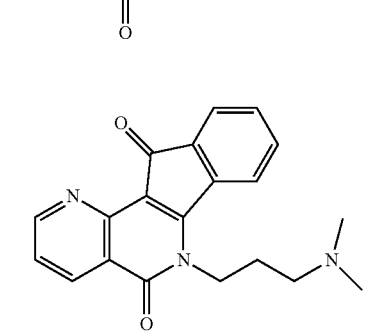

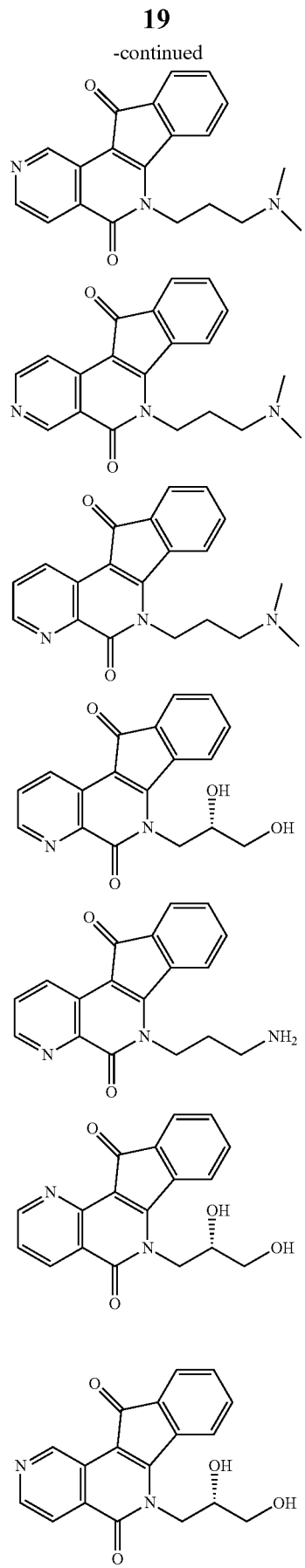
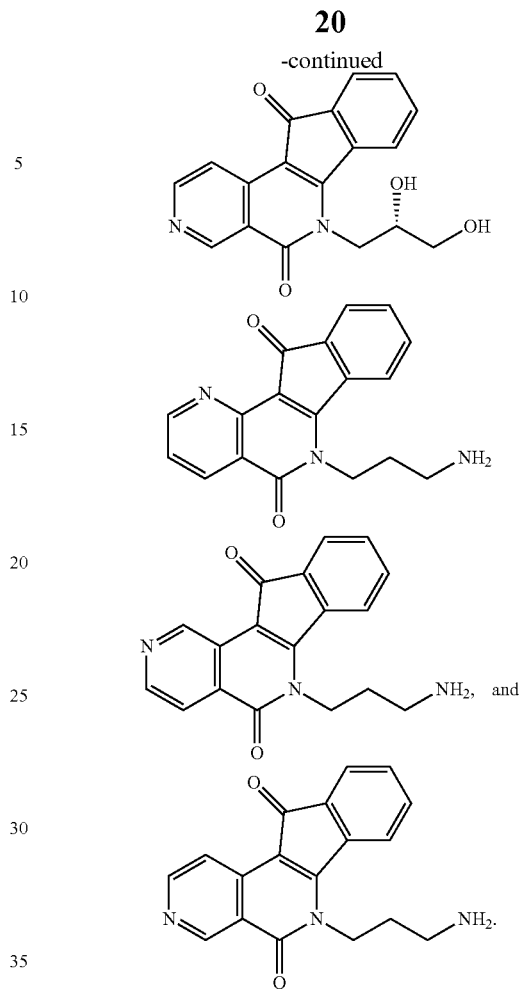

It is to be understood that all possible combinations of the various genera and subgenera of each of A, B, C, D, $R^1$, $R^2$, $R^3$, $R^4$ and $R^5$ described herein represent additional illustrative embodiments of compounds of the invention described herein. It is also to be understood that each of those additional illustrative embodiments of compounds may be used in any of the compositions, methods, and/or uses described herein.

In some embodiments, the invention is related to a pharmaceutical composition comprising one or more compounds disclosed herein, or a pharmaceutically acceptable salt thereof, together with one or more diluents, excipients or carriers.

In some embodiments, the invention is related to a pharmaceutical composition comprising one or more compounds disclosed herein, or a pharmaceutically acceptable salt thereof, together with one or more diluents, excipients or carriers, for use as a medicament.

In some embodiments, the invention is related to a pharmaceutical composition comprising one or more compounds disclosed herein, or a pharmaceutically acceptable salt thereof, together with one or more diluents, excipients or carriers, for use as a treatment for a cancer.

In some embodiments, the invention is related to a method for treating cancer comprising the step of administering a therapeutically effective amount of one or more compounds disclosed in any of the embodiments, and one or more carriers, diluents, or excipients, to a patient in need of relief from said cancer.

In some embodiments, the invention is related to a method for treating cancer comprising the step of administering a therapeutically effective amount of one or more compounds disclosed in any of the embodiments in combination with one or more other compounds of the same or different mode of action, and one or more carriers, diluents, or excipients, to a patient in need of relief from said cancer.

In another embodiment, pharmaceutical compositions containing one or more of the compounds are also described herein. In one aspect, the compositions include a therapeutically effective amount of the one or more compounds for treating a patient with cancer. It is to be understood that the compositions may include other component and/or ingredients, including, but not limited to, other therapeutically active compounds with the same or different modes of action, and one or more carriers, diluents, excipients, and the like. In another embodiment, methods for using the compounds and pharmaceutical compositions for treating patients with cancer are also described herein. In one aspect, the methods include the step of administering one or more of the compounds and/or compositions described herein to a patient with cancer. In another aspect, the methods include administering a therapeutically effective amount of the one or more compounds and/or compositions described herein for treating patients with cancer.

In addition, it is appreciated herein that the compounds described herein may be used in combination with other compounds that are administered to treat other symptoms of cancer, such as compounds administered to relieve pain, nausea, vomiting, and the like.

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein.

The strategy used to synthesize aza-A-ring indenoisoquinolines centered on the preparation of key tetracyclic lactone precursors, such as 13. An advantage of this approach is that several azaindenoisoquinolines that differ at the lactam nitrogen side chain can be prepared using a divergent pathway from a single common intermediate. It was anticipated that the location of the nitrogen atom in the azaphthalide intermediates (e.g. 8) could be controlled by regioselective reactions of carbonyl groups attached to C-2 and C-4 as opposed to C-3 of the pyridine ring system. This would ultimately dictate the locations of the nitrogen in the final products.

The lactone 13 with a nitrogen atom in the 1-position was made by the route outlined in Scheme 2. Quinolinic acid anhydride 7 was regioselectively reduced with NaBH$_4$ in THF-AcOH, and the intermediate hydroxyacid was cyclized under the acidic reaction conditions to yield 4-azaphthalide (8). The 55% yield of 8 obtained this way was superior to the 15-25% yields reported by LAH reduction of 7 followed by sublimation. The latter was monobrominated with NBS to afford 9, which was then hydrolyzed to provide 4-aza-3-hydroxyphthalide (10). Condensation of 10 with phthalide (11) under basic conditions involving a Dieckmann condensation sequence generated indanedione intermediate 12, which was treated with refluxing Ac$_2$O to close the B-ring, yielding the lactone 13.

The synthesis of lactone 21 began with isonicotinic acid (14, Scheme 3). After the formation of N-phenyl amide 15, lithiation and functionalization with DMF provided lactam 16. Reduction of lactam 16 with NaBH$_4$ in MeOH delivered 17, and lactonization in aqueous HCl yielded azapthalide 18. From this point, oxidation with NBS to afford 19, hydrolysis to yield 20, and condensation of 20 with 11 followed by cyclization of the resulting intermediate in refluxing Ac$_2$O produced the final product 21. The synthesis of lactone 26 was accomplished according to our previously published procedure (Scheme 4) (Beck, D. E., et al, *J. Med. Chem.* 2015, 58, 3997-4015).

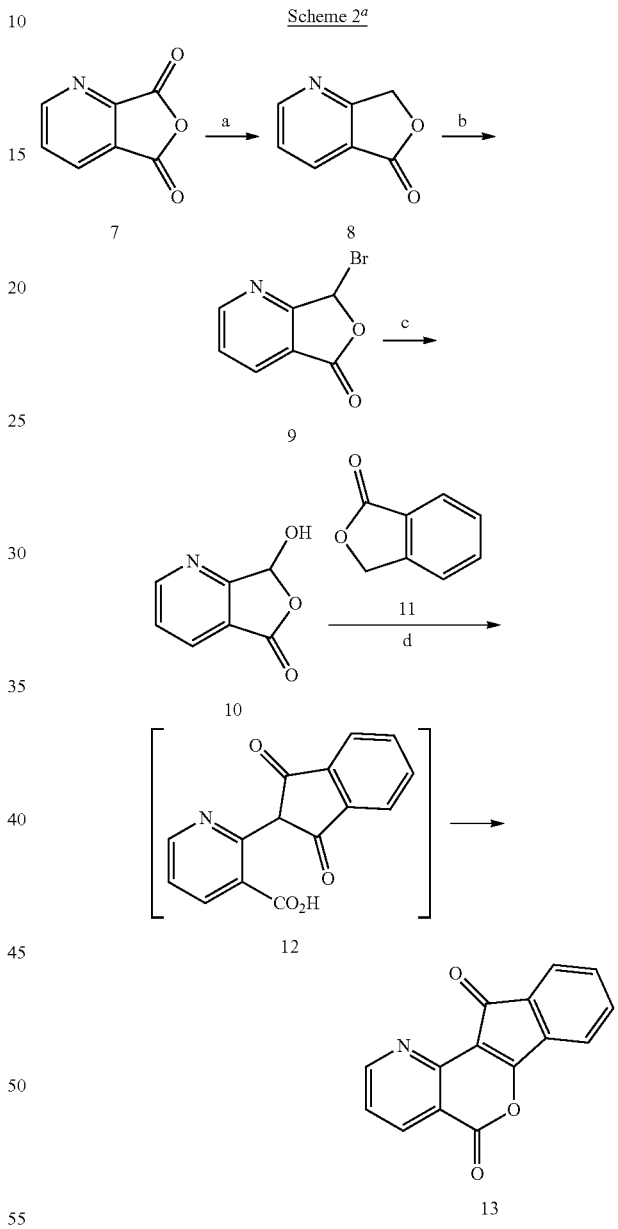

[a]Reagents and conditions: (a) i. NaBH$_4$, THF, AcOH, 15° C., 4 h; ii. Ac$_2$O, AcOH, 100° C., 3 h; (b) NBS, AIBN, CCl$_4$, reflux, 2 h; (c) H$_2$O, reflux, 2 h; (d) i. NaOMe, MeOH, EtOAc, reflux, 15 h, then HCl; ii. Ac$_2$O, reflux, 6 h.

Anhydride 22 was reduced with NaBH$_4$ in PhMe-DMF, and the reduction product was cyclized in refluxing 5 M HCl to provide phthalide 23 (Scheme 4). Phthalide 23 was subjected to radical bromination, and hydrolysis of the product (24) produced 3-hydroxyphthalide 25. Phthalide (11) and 3-Hydroxyphthalide 25 were condensed under basic conditions, and the unisolated intermediate was cyclized in refluxing Ac$_2$O to yield lactone 26.

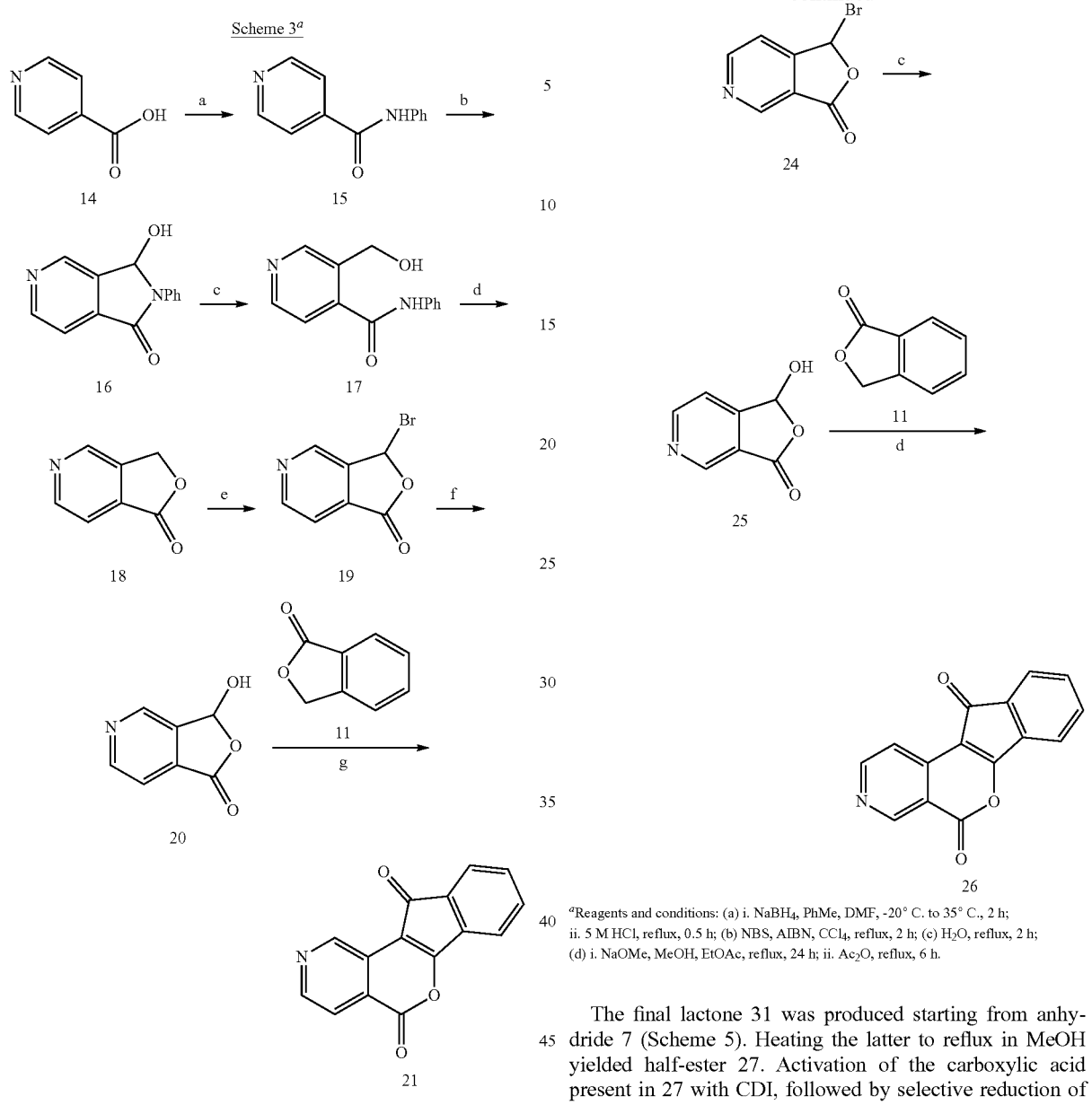

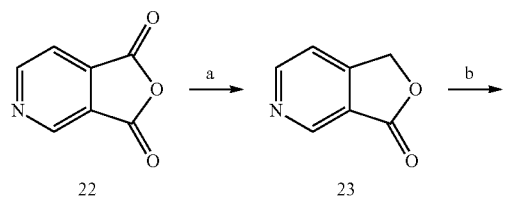

[a]Reagents and conditions: (a) i. NaBH$_4$, PhMe, DMF, -20° C. to 35° C., 2 h; ii. 5 M HCl, reflux, 0.5 h; (b) NBS, AIBN, CCl$_4$, reflux, 2 h; (c) H$_2$O, reflux, 2 h; (d) i. NaOMe, MeOH, EtOAc, reflux, 24 h; ii. Ac$_2$O, reflux, 6 h.

The final lactone 31 was produced starting from anhydride 7 (Scheme 5). Heating the latter to reflux in MeOH yielded half-ester 27. Activation of the carboxylic acid present in 27 with CDI, followed by selective reduction of the mixed anhydride and cyclization yielded 7-azaphthalide 28. Oxidation with NBS afforded 29, followed by hydrolysis of the bromide to yield 30. Condensation of 30 with phthalide (11) as before gave the desired lactone 31. The regioselectivities of the key carbonyl reactions observed in Schemes 2, 4, and 5 (7→8, 22→23, and 7→27) are the result of the greater reactivity of carbonyl substituents at C-2 and C-4 vs. C-3 on the pyridine ring, which is a consequence of the greater electronegativity of the nitrogen atom vs. a carbon atom.

Lactones 13, 21, 26, and 31 were condensed with primary amines 32-35 in CHCl$_3$, with or without MeOH as a co-solvent, to yield aza-A-ring indenoisoquinolines 36-39, 40-43, 44-47, and 48-51 (Schemes 6 and 7). Lastly, lactones 13, 21, 26, and 31 were each condensed with N-Boc-1,3-diaminopropane (52), and the resulting intermediates 53-56 were deprotected with 5 N HCl in MeOH and CHCl$_3$ to yield aza-A-ring indenoisoquinoline dihydrochloride salts 57-60 (Scheme 8).

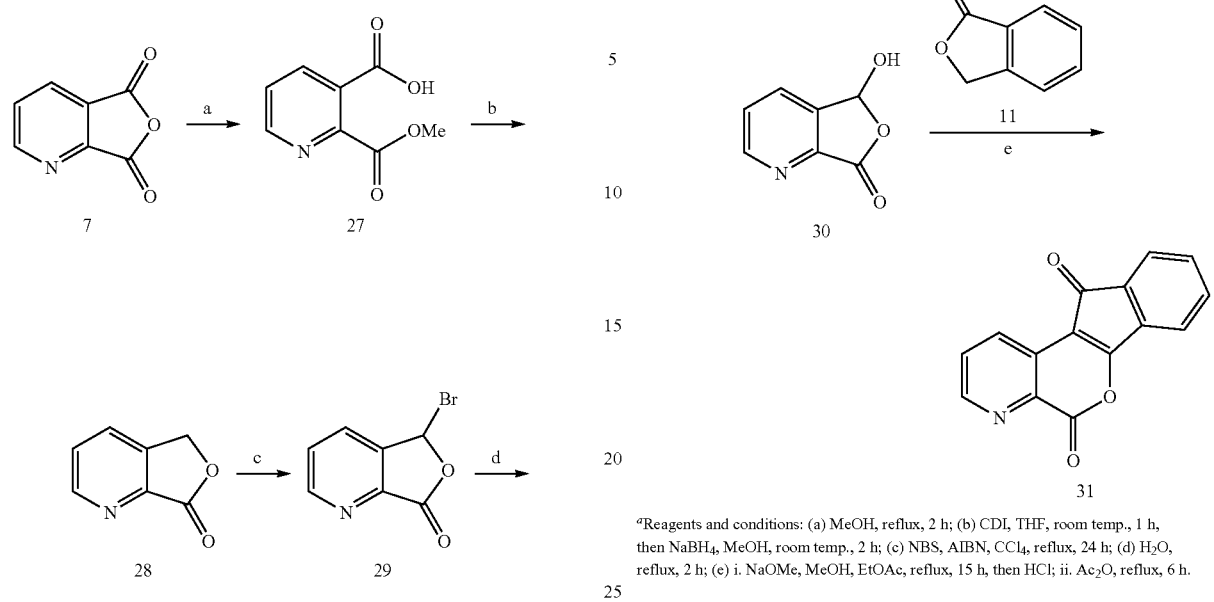
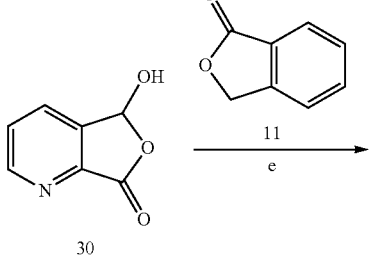
Scheme 5[a]
[a]Reagents and conditions: (a) MeOH, reflux, 2 h; (b) CDI, THF, room temp., 1 h, then NaBH₄, MeOH, room temp., 2 h; (c) NBS, AIBN, CCl₄, reflux, 24 h; (d) H₂O, reflux, 2 h; (e) i. NaOMe, MeOH, EtOAc, reflux, 15 h, then HCl; ii. Ac₂O, reflux, 6 h.
Scheme 6[a]
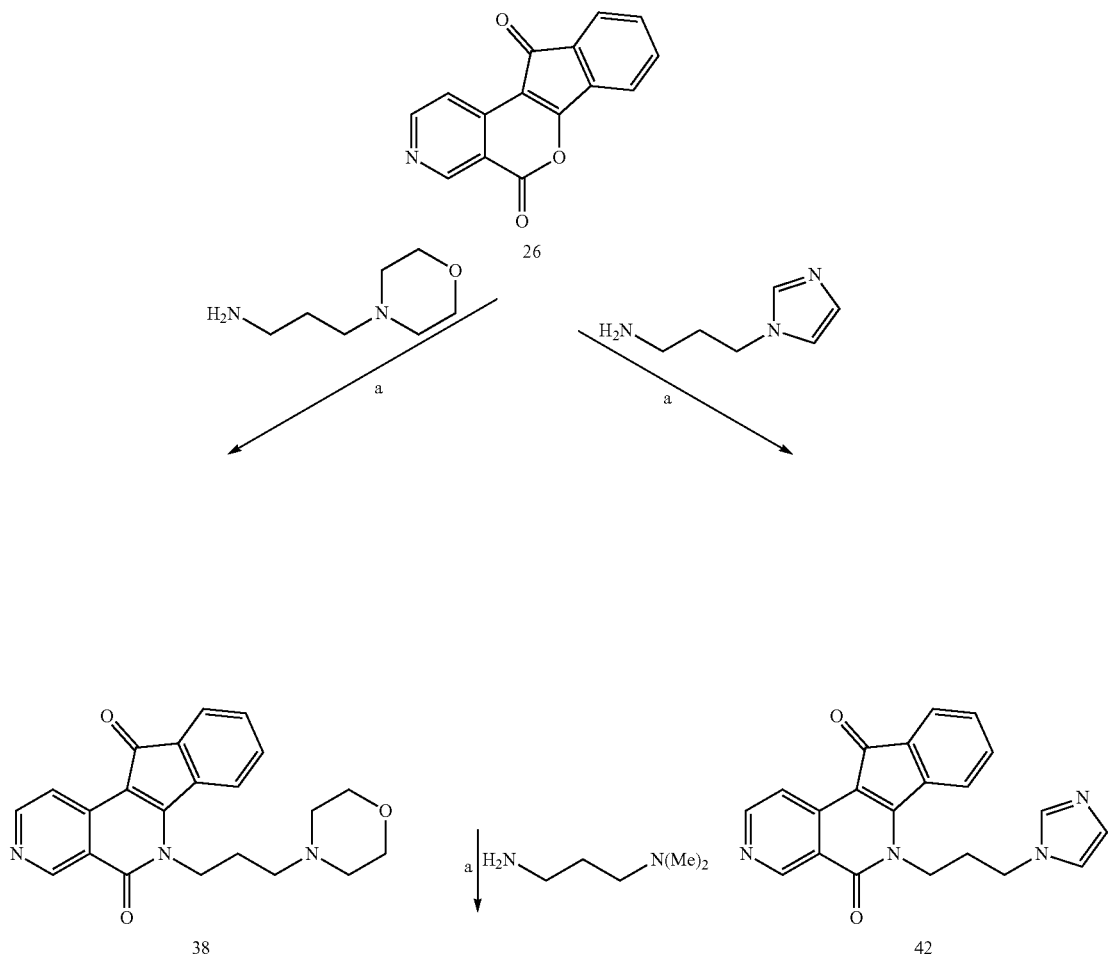

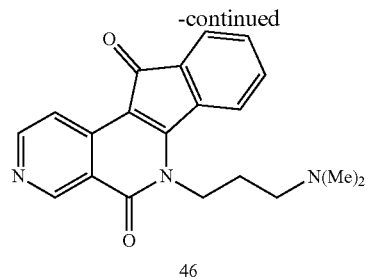
46
*Reagents and conditions: (a) CHCl₃, reflux.
Scheme 7*
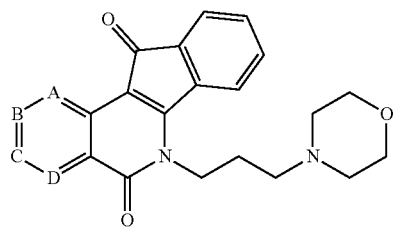
36: A = N, B, C, D = CH
37: B = N, A, C, D = CH
38: C = N, A, B, D = CH
39: D = N, A, B, C = CH
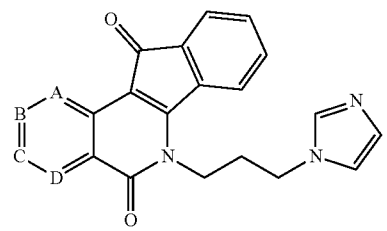
40: A = N, B, C, D = CH
41: B = N, A, C, D = CH
42: C = N, A, B, D = CH
43: D = N, A, B, C = CH
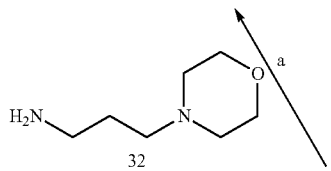
32
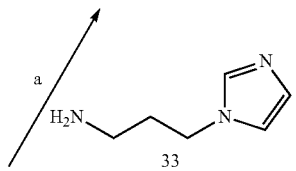
33
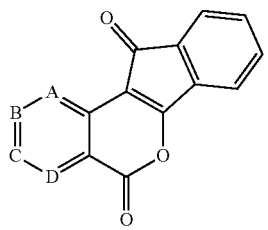
13: A = N, B, C, D = CH
21: B = N, A, C, D = CH
26: C = N, A, B, D = CH
31: D = N, A, B, C = CH
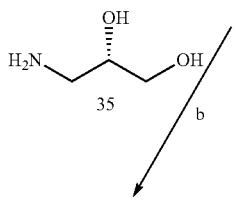
35
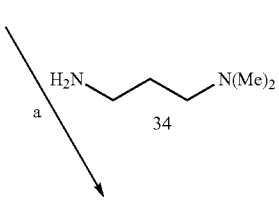
34

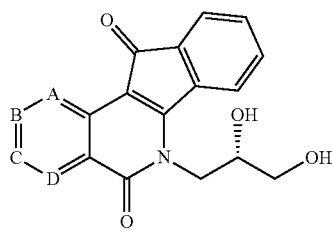

48: A = N, B, C, D = CH
49: B = N, A, C, D = CH
50: C = N, A, B, D = CH
51: D = N, A, B, C = CH

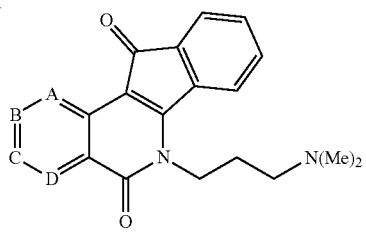

44: A = N, B, C, D = CH
45: B = N, A, C, D = CH
46: C = N, A, B, D = CH
47: D = N, A, B, C = CH

[a]Reagents and conditions: (a) CHCl$_3$, reflux, 15 h; (b) CHCl$_3$, MeOH, reflux or room temperature.

Scheme 8[a]

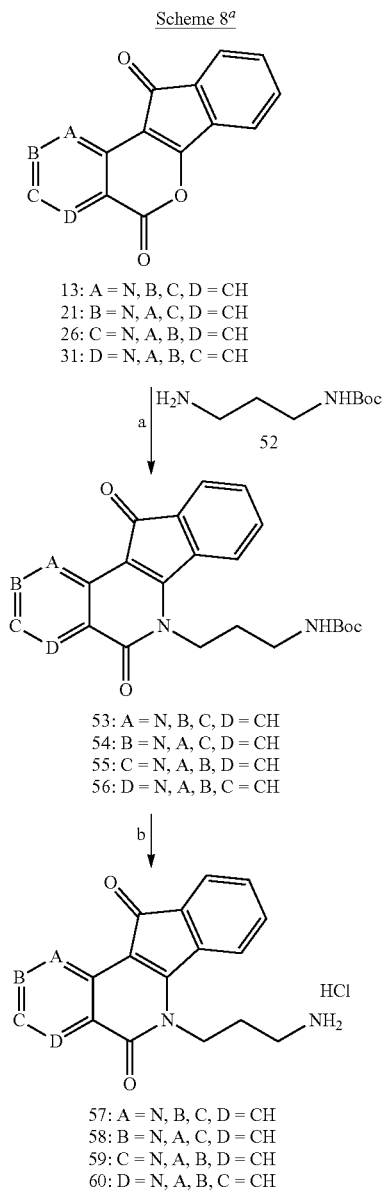

[a]Reagents and conditions: (a) CHCl$_3$, reflux, 24 h; (b) 5 N HCl in MeOH, CHCl$_3$, 6 h.

Biological Activity Assay and Results
Topoisomerase I-Mediated DNA Cleavage Reactions.

A 3'-[$^{32}$P]-labeled 117-bp DNA oligonucleotide was prepared as previously described. The oligonucleotide contains previously identified Top1 cleavage sites in 161-bp pBluescript SK(−) phagemid DNA. Approximately 2 nM radiolabeled DNA substrate was incubated with recombinant Top in 20 μL of reaction buffer [10 mM Tris-HCl (pH 7.5), 50 mM KCl, 5 mM MgCl$_2$, 0.1 mM EDTA, and 15 μg/mL BSA] at 25° C. for 20 min in the presence of various concentrations of test compounds. The reactions were terminated by adding SDS (0.5% final concentration) followed by the addition of two volumes of loading dye (80% formamide, 10 mM sodium hydroxide, 1 mM sodium EDTA, 0.1% xylene cyanol, and 0.1% bromophenol blue). Aliquots of each reaction mixture were subjected to 20% denaturing PAGE. Gels were dried and visualized by using a phosphoimager and ImageQuant software (Molecular Dynamics). Cleavage sites are numbered to reflect actual sites on the 117 bp oligonucleotide (Dexheimer, T. S., et al, Nat. Protoc. 2008, 3, 1736-1750).

Recombinant TDP1 Assay.

A 5'-[$^{32}$P]-labeled single-stranded DNA oligonucleotide containing a 3'-phosphotyrosine (N14Y) was incubated at 1 nM with 10 pM recombinant TDP1 in the absence or presence of inhibitor for 15 min at room temperature in the LMP1 assay buffer containing 50 mM Tris HCl, pH 7.5, 80 mM KCl, 2 mM EDTA, 1 mM DTT, 40 μg/mL BSA, and 0.01% Tween-20[18]. Reactions were terminated by the addition of 1 volume of gel loading buffer [99.5% (v/v) formamide, 5 mM EDTA, 0.01% (w/v) xylene cyanol, and 0.01% (w/v) bromophenol blue]. Samples were subjected to a 16% denaturing PAGE with multiple loadings at 12-min intervals. Gels were dried and exposed to a PhosphorImager screen (GE Healthcare). Gel images were scanned using a Typhoon 8600 (GE Healthcare), and densitometry analyses were performed using ImageQuant software (GE Healthcare).

Recombinant TDP2 Assay.

TDP2 reactions were carried out as described previously with the following modifications (Gao, R., et al., J. Biol. Chem. 2012, 287, 30842-30852). The 19-mer single-stranded oligonucleotide DNA substrate containing a 5'-phosphotyrosine (Y19, α$^{32}$P-cordycepin-3'-labeled) was incubated at 1 nM with 25 pM recombinant human TDP2 in the absence or presence of inhibitor for 15 min at room temperature in the LMP2 assay buffer containing 50 mM Tris-HCl, pH 7.5, 80 mM KCl, 5 mM MgCl$_2$, 0.1 mM EDTA, 1 mM DTT, 40 μg/mL BSA, and 0.01% Tween 20. Reactions were terminated and treated similarly to recombinant TDP1 reactions.

Figure 1B:
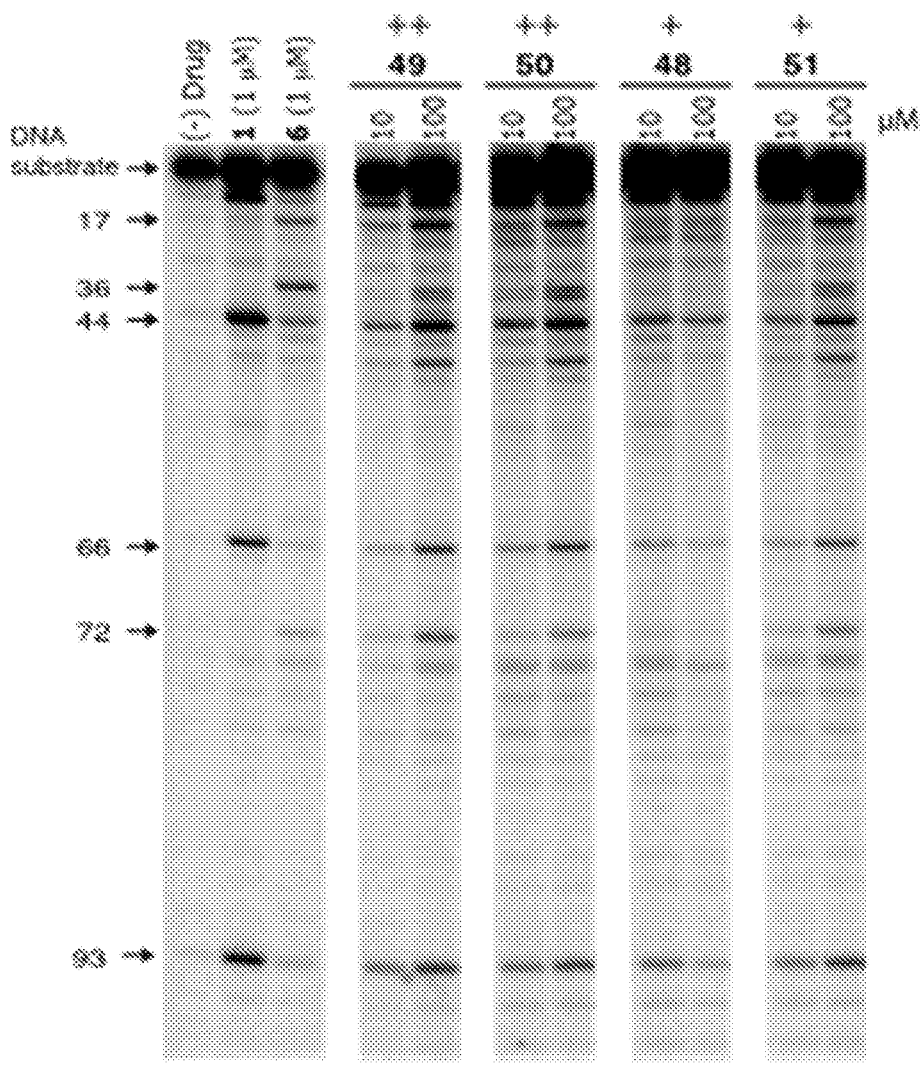
FIG. 1B is a gel showing the results of Top1-mediated DNA cleavage assay of concentration-response for compounds 48-51.

The Top1-mediated DNA cleavage assay was used to measure Top1 inhibitory activity. This assay measures the ability of the compound to stabilize DNA cleavage in a 3'-[$^{32}$P]-labeled DNA substrate via Top1 poisoning. Putative Top1 poisons are tested at 0.1, 1, 10, and 100 µM concentrations, alongside positive controls camptothecin (CPT) (1) and MJ-III-65 (4) at 1 µM concentration. A representative gel is shown in FIGS. 1A and 1B. The assay results are summarized in Table 1.

The new indenoisoquinolines were evaluated for cancer cell growth inhibitory activities. The National Cancer Institute's NCI-60 cytotoxicity assay measures the ability of test agents to inhibit the growth of approximately 60 different cancer cell lines. In the initial single-dose assay, cells are treated with a 10 µM dose of test agent. The growth of treated cells versus untreated cells is then compared. If a test

TABLE 1

Top1 Poisoning and TDP1 and TDP2 Inhibitory Activities of Aza-A-Ring Indenoisoquinolines

|  | Compound | Top 1[a] | TDP1[b] | TDP2[c] | Mean Growth %[d] | Side Chain |
|---|---|---|---|---|---|---|
|  | 1 | ++++ | N.A.[e] | N.A. | N.A. |  |
| 1-aza | 36 | ++ | >111 | >111 | 87.9 | morpholinopropyl |
|  | 40 | ++ | >111 | >111 | 83.6 | imidazolylpropyl |
|  | 44 | ++ | 90 | >111 | 44.4 | dimethylaminopropyl. |
|  | 48 | + | >111 | >111 | 100 | dihydroxypropyl |
|  | 57 | ++ | 43, 63 (n = 2) | >111 | N.T. | aminopropyl |
| 2-aza | 37 | +++ | >111 | >111 | N.T. | morpholinopropyl |
|  | 41 | ++ | >111 | >111 | 67.8 | imidazolylpropyl |
|  | 45 | ++ | 63 | 37 | −8.83 | dimethylaminopropyl |
|  | 49 | + | >111 | >111 | 85.5 | dihydroxypropyl |
|  | 58 | ++ | 19, 30 (n = 2) | ~111 | N.T. | aminopropyl |
| 3-aza | 38 | ++ | >111 | >111 | N.T. | morpholinopropyl |
|  | 42 | + | >111 | >111 | 47.5 | imidazolylpropyl |
|  | 46 | ++ | 63 | 80 | −9.25 | dimethylaminopropyl |
|  | 50 | ++ | >111 | >111 | N.T. | dihydroxypropyl |
|  | 59 | 0/+ | 30, 48 (n = 2) | ~111 | N.T. | aminopropyl |
| 4-aza | 39 | +++ | >111 | >111 | 42.9 | morpholinopropyl |
|  | 43 | +++ | >111 | >111 | 49.6 | imidazolylpropyl |
|  | 47 | +++ | ~111 | >111 | 5.45 | dimethylaminopropyl |
|  | 51 | + | >111 | >111 | 61.7 | dihydroxypropyl |
|  | 60 | ++ | 60, >111 (n = 2) | >111 | 12.2 | aminopropyl |

[a]Compound-induced DNA cleavage due to Top1 poisoning, with scores given according to the following system based on the activity of 1 µM 1: 0, no activity; +, between 20 and 50%activity; ++, between 50 and and 75% activity; +++, between 75 and 95% activity; ++++, equal activity; ++++(+), greater activity. [b]IC$_{50}$ values for the inhibition of TDP1 (µM). [c]IC$_{50}$ values for the inhibition of TDP2 (µM). [d]The mean-graph midpoint of the percent growth of 60 human cancer cell lines treated with 10 µM drug concentration for 48 h relative to no-drug control, and relative to the time zero number of cells. [e]Not available. [f]Not tested because the compound was not accepted for evaluation by the National Cancer Institute, Developmental Therapeutics Program.

Figure 2:
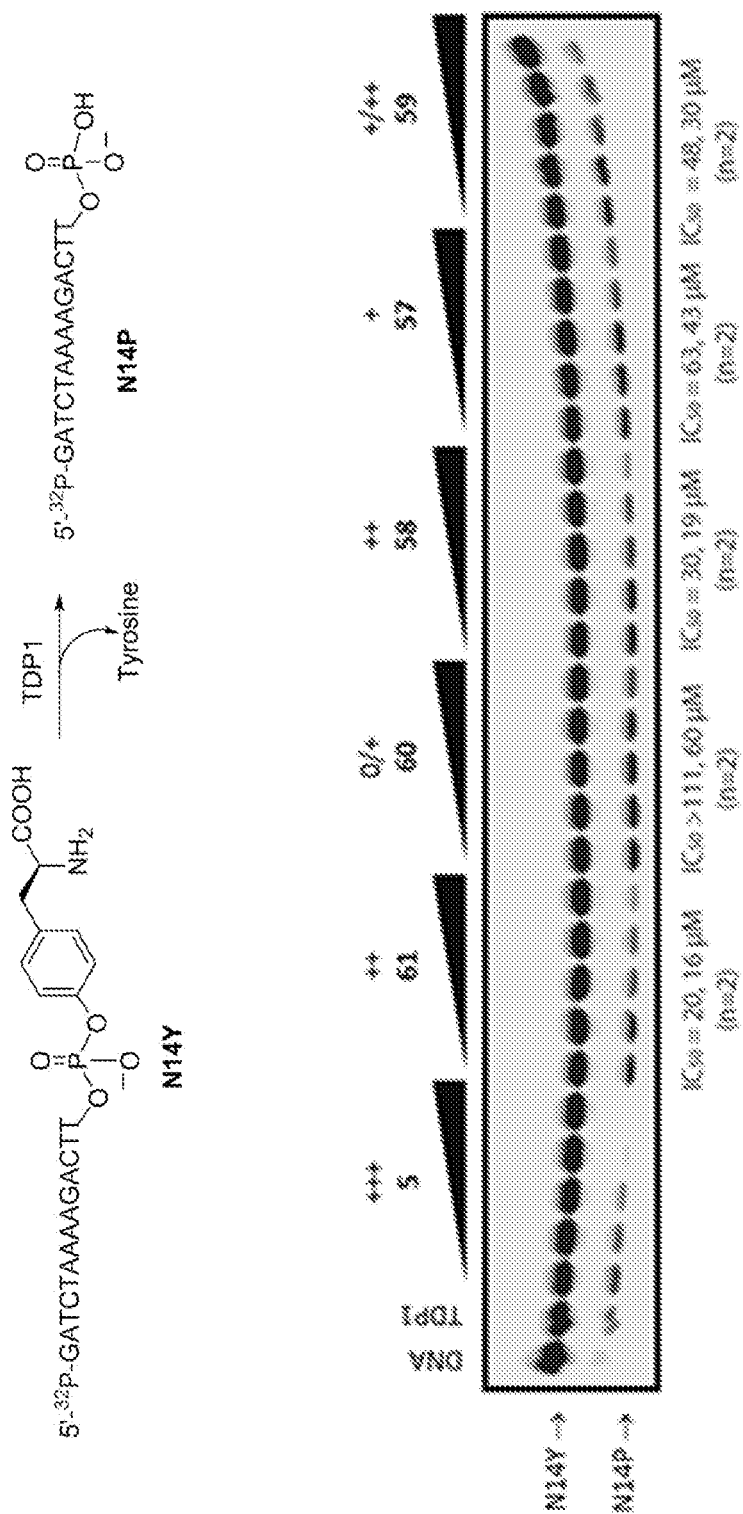
FIG. 2 shows the gel of experimental samples from the TDP1 inhibition assay. The concentrations of positive controls 5 and 61 and test compounds were 1.4, 4.1, 12.3, 37, and 111 M (left to right). N14Y is 5'-end labeled DNA oligonucleotide with 3' phosphotyrosyl, and N14P is 5'-end labeled DNA oligonucleotide. Gel-based assays are commonly acquired twice for each compound. The "+"-based scoring system rubric is as follows: 0, $IC_{50} \geq 111$ μM; +, $IC_{50}$ 37-111 μM; ++, $IC_{50}$ 12-37 μM; +++, $IC_{50}$ 1-12 μM; ++++, and $IC_{50} \leq 1$ μM.

TDP1 is involved in the repair of DNA damage that results from the action of Top1 poisons, which induce the formation of DNA-protein adducts that include a 3'-phosphotyrosyl linkage. The TDP1 inhibition assay assesses a test agent's ability to inhibit the enzyme-induced cleavage of a 5'-$^{32}$P, 3'-phosphotyrosyl-DNA oligonucleotide, called N14Y. Cleavage of the phosphodiester bond between the 3'-phosphate and tyrosine releases phosphotyrosine from the DNA oligonucleotide. The enzyme-processed DNA oligonucleotide lacking its 3'-phosphotyrosyl moiety is designated N14P. A schematic representation of the assay and a representative gel are shown in FIG. 2, and the TDP1 screening results are listed in Table 1.

Figure 3:
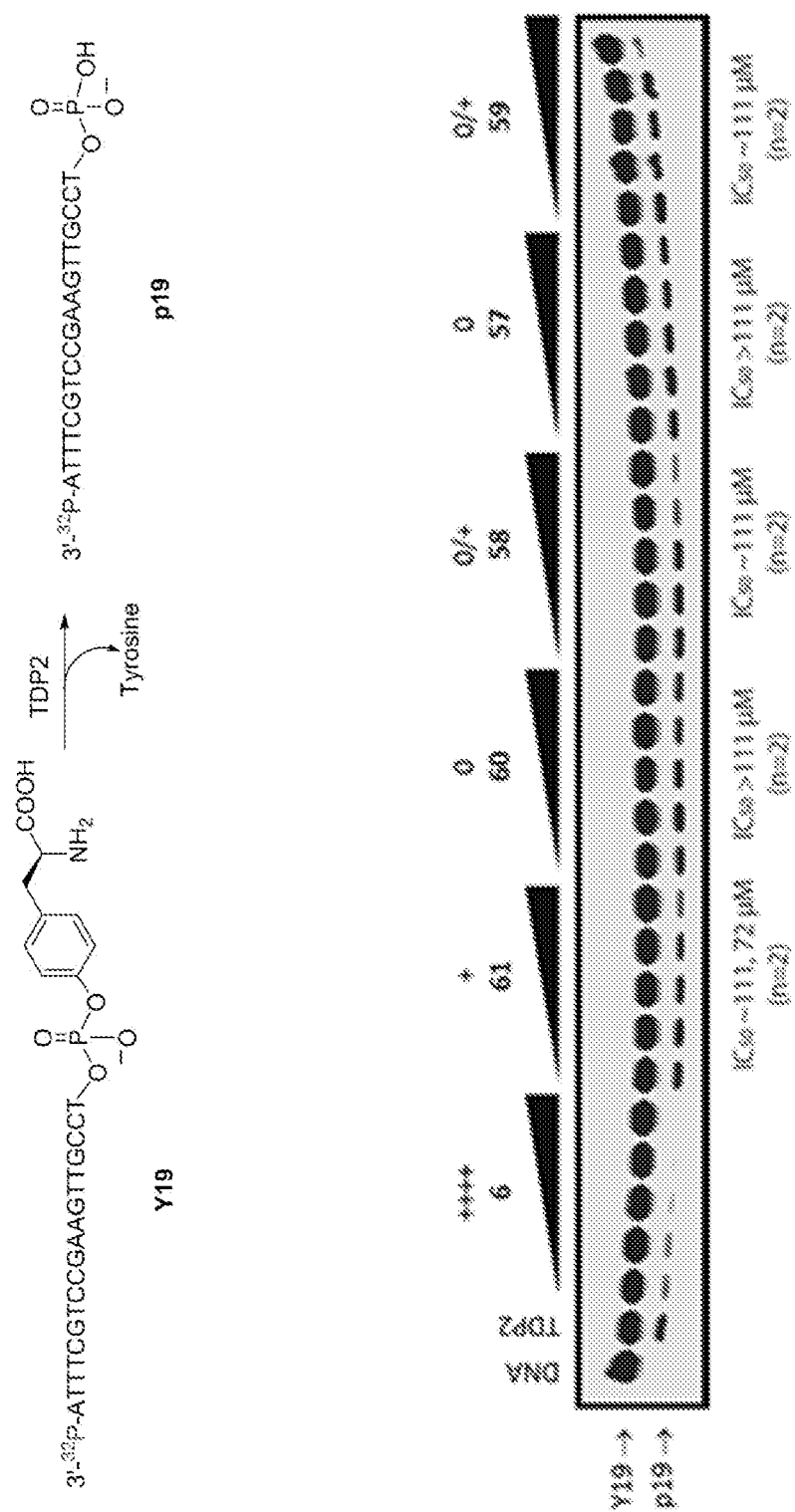
FIG. 3 shows the gel of experimental samples from the TDP2 inhibition assay. The concentrations of positive control 6 were 0.006, 0.017, 0.05, 0.15, and 0.46 μM and the concentrations of 61 and the test compounds were 0.46, 1.4, 4.1, 12.3, 37, 111 μM (left to right). The TDP2 substrate Y19 corresponds to a 3'-end labeled DNA-oligonucleotide with a 5' phosphotyrosyl, and the TDP2 product p19 corresponds to a 3'-end labeled DNA-oligonucleotide with a 5' phosphate group. The "+"-based scoring system rubric is the same as that for the TDP1 assay (see FIG. 2 caption).

TDP2, as opposed to TDP1, cleaves the phosphotyrosyl linkage in 5'-phosphotyrosyl-DNA oligonucleotides. Both a schematic representation of the assay and a representative gel are displayed in FIG. 3. TDP2 inhibitory activity observed is summarized in Table 1 as well.

agent induces a sufficiently low mean growth percent, it is promoted to five-dose testing to determine a mean graph midpoint (MGM) GI$_{50}$ value. In five-dose testing, cells are treated with test agent concentrations ranging from 10$^{-8}$ to 10$^{-4}$ M. The concentration required to achieve 50% growth inhibition in a particular cell line is calculated. In situations in which this value is greater than 100 µM or less than 0.01 µM, it is recorded as 100 µM and 0.01 µM, respectively. The values for each of the tested cell lines are averaged to obtain a mean graph midpoint (MGM) GI$_{50}$ value. MGM GI$_{50}$ values are often, but not always, determined from two separate rounds (Table 1). On the basis of the one-concentration testing, the most active compounds 45 (−8.83%), 46 (−9.25%), 47 (5.45%), and 60 (12.2%) were further tested in the five-dose cytotoxicity assay (Table 2).

TABLE 2

Antiproliferative Activities of Aza A-Ring Indenoisoquinolines

| | Cytotoxicity (GI$_{50}$, μM) | | | | | | | | |
|---|---|---|---|---|---|---|---|---|---|
| compd | Lung, HOP-62 | Colon, HCT-116 | CNS, SF-539 | Melanoma UACC-62 | Ovarian, OVCAR-3 | Renal, SN12C | Prostate, DU-145 | Breast, MCF7 | MGM[a] |
| 1 | 0.01 | 0.03 | 0.01 | 0.01 | 0.22 | 0.02 | 0.01 | 0.01 | 0.0405 |
| 45 | 0.398 | 0.245 | 0.380 | 0.309 | 1.10 | 0.288 | 0.490 | 0.245 | 0.437 |
| 46 | 0.871 | 0.380 | 0.708 | 1.23 | 2.00 | 0.955 | 0.977 | 0.331 | 0.977 |
| 47 | 1.26 | 0.437 | 0.851 | 1.29 | 2.40 | 1.12 | 1.91 | 0.363 | 1.26 |
| 60 | 1.45 | 0.537 | 1.38 | 1.35 | 2.29 | 1.12 | 1.91 | 0.417 | 1.51 |

[a]Mean graph midpoint of growth inhibition from 5 dose assay, ranging from 10$^{-8}$-10$^{-4}$M.

Examples of Compound Preparation

Reactions were monitored by silica gel analytical thin-layer chromatography, and 254 nm UV light was used for visualization. All yields refer to isolated compounds. Unless otherwise stated, chemicals and solvents were of reagent grade and used as obtained from commercial sources without further purification. Melting points were determined using capillary tubes and are uncorrected. $^1$H Nuclear magnetic resonance spectroscopy was performed using a 300 MHz spectrometer. Infrared spectra were obtained using an FTIR spectrometer. Mass spectral analyses were performed at the Purdue University Campus-Wide Mass Spectrometry Center. HPLC analyses were performed on a Waters 1525 binary HPLC pump/Waters 2487 dual λ absorbance detector system, using a 5 μm C18 reversed phase column and UV detection at 254 nm. HPLC purities of all tested compounds were estimated from the major peak areas, which were ≥95% of the combined total peak areas.

4-Azaphthalide (8)

NaBH$_4$ (1.14 g, 33.5 mmol) was added to a solution of quinolinic acid anhydride (7, 5.0 g, 33.5 mmol) in THF (35 mL) at 15° C. under argon. Acetic acid (4 g, 67 mmol) was added dropwise and the resulting mixture was stirred at 15° C. for 4 h. The solvent was removed in vacuo. The residue was dissolved in acetic acid (13.5 mL) and acetic anhydride (13.5 mL) and the resulting solution was stirred for 3 h at 100° C. The mixture was concentrated in vacuo and the residue was dissolved in a solution of H$_2$O (35 mL)+NaCl (6.7 g). The water phase was extracted with CHCl$_3$ (3×40 mL) and the combined organic layers were concentrated. Recrystallization from i-PrOH yielded compound 8 (2.5 g, 55%) as a light yellow solid: mp 123-125° C. IR (KBr) 1778, 1567, 1423, 1355, 1000, 743 cm$^{-1}$; $^1$H NMR (300 MHz, CDCl$_3$) δ 8.87 (dd, J=1.5, 4.9 Hz, 1H), 8.22 (dd, J=1.5, 7.7 Hz, 1H), 7.50 (dd, J=5.0, 7.8 Hz, 1H), 5.33 (s, 2H); ESIMS m/z (rel intensity) 136 (MH$^+$, 100).

4-Aza-3-bromophthalide (9)

Compound 8 (1.0 g, 7.40 mmol) was heated at reflux with NBS (1.44 g, 8.1 mmol) and AIBN (20 mg) in dry CCl$_4$ (40 mL) for 2 h. The reaction mixture was cooled to room temperature, the succinate salts were filtered off, and the filtrate was concentrated and purified by silica gel flash column chromatography (75:25 EtOAc-hexanes) to afford product 9 (1.4 g 87%) as a colorless syrup. IR (film) 1782, 1594, 1428, 986, 667 cm$^{-1}$; $^1$H NMR (CDCl$_3$, 300 MHz) δ 8.99 (dd, J=1.4, 4.9 Hz, 1H), 8.26 (dd, J=1.4, 7.8 Hz, 1H), 7.59 (dd, J=4.8, 7.8 Hz, 1H), 7.38 (s, 1H); CIMS m/z (rel intensity) 214 (MH$^+$, 100).

4-Aza-3-hydroxyphthalide (10)

Compound 9 (1.4 g, 6.5 mmol) was heated at reflux in H$_2$O (40 mL) for 2 h before the solvent was evaporated to afford compound 10 (0.9 g, 91%) as a light yellow solid: mp 209-211° C. IR (KBr) 3145, 1784, 1721, 1619, 1214, 1076, 765 cm$^{-1}$; $^1$H NMR (CDCl$_3$, 300 MHz) δ 8.94 (dd, J=1.5, 4.9 Hz, 1H), 8.29 (dd, J=1.4, 7.8 Hz, 1H), 7.69 (dd, J=4.9, 7.7 Hz, 1H), 6.61 (s, 1H); ESIMS m/z (rel intensity) 152 (MH$^+$, 100).

General Procedure A.

The appropriate aza-3-hydroxyphthalides (0.5 g, 3 mmol) and phthalide (11, 0.41 g, 3.1 mmol) were diluted in EtOAc (15 mL). Sodium metal (0.35 g, 15 mmol) was dissolved in MeOH (30 mL) and the solution was added to reaction mixture. The solution was heated at reflux for 24 h, cooled to room temperature, acidified with 37% HCl (3-4 mL), and concentrated. The obtained solid was diluted with Ac$_2$O (20 mL) and the mixture was heated at reflux for 6 h. The solution was concentrated, diluted with CHCl$_3$ (100 mL), and washed with sat. NaHCO$_3$ (3×50 mL). The organic layer was washed with sat. NaCl (75 mL), dried over Na$_2$SO$_4$, concentrated and purified by silica gel column chromatography (9:1 CHCl$_3$-hexanes) to yield product 13, 21, 26 or 31.

1-Azaindeno[1,2-c]isochromene-5,11-dione (13)

Following general procedure A, 13 (0.125 g, 15%) was obtained as an orange-red solid: mp 167-168° C. IR (KBr) 1754, 1712, 1492, 998, 695 cm$^{-1}$; $^1$H NMR (CDCl$_3$, 300 MHz) δ 8.94 (d, J=4.5 Hz, 1H), 8.24 (d, J=7.0 Hz, 2H), 7.53 (m, 4H); ESIMS m/z (rel intensity) 250 (MH$^+$, 100); HRES-IMS calcd for C$_{15}$H$_8$NO$_3$ 250.0504 (MH$^+$), found 250.0501.

N-Phenylisonicotinamide (15)

A solution of isonicotinic acid (14, 5.0 g, 40.6 mmol) in thionyl chloride (40 mL) was heated at reflux for 2 h. After completion of the reaction, thionyl chloride was removed under reduced pressure. THF (50 mL), K$_2$CO$_3$ (16.8 g, 121.9 mmol) and aniline (3.78 g, 40.6 mmol) were added to the residue and the reaction mixture was stirred at room temperature for 24 h. The reaction mixture was diluted with water (100 mL) and extracted with EtOAc (2×100 mL). The combined organic layer was concentrated and the residue was recrystallized from EtOAc-hexanes (60:40) to afford the product 15 (8.0 g, 99%) as a light yellow solid: mp 166-168° C. IR (KBr) 1344, 1653, 1465, 665 cm$^{-1}$; $^1$H NMR (DMSO-d$_6$, 300 MHz) δ 10.49 (s, 1H), 8.78 (m, 2H), 7.86 (m, 2H), 7.78 (m, 2H), 7.39 (t, J=8.0 Hz, 2H), 7.15 (t, J=6.5 Hz, 1H).

3-Hydroxy-2-phenyl-2,3-dihydro-1H-pyrrolo[3,4-c]pyridin-1-one (16)

A 2.5 M n-BuLi solution in hexanes (17.8 mL, 44.4 mmol) was added to a solution of 15 (4.0 g, 20 mmol) in dry THF (120 mL) at −78° C. The solution was held at −78° C. for 0.5 h and then allowed to rise to 0° C. and kept at 0° C. for 6 min. The mixture was cooled to −78° C. and DMF (2.94 mL, 40.4 mmol) was added. After 1 h at −78° C., the reaction mixture was warmed to 0° C. and kept at 0° C. for 1 h. $H_2O$ (40 mL) was added, the organic layer was separated, and the water layer was extracted with $CHCl_3$ (2×40 mL). The combined organic layer was dried over $Na_2SO_4$, concentrated, and purified by silica gel flash column chromatography (60:40 EtOAc-hexanes) to afford compound 16 (3.0 g, 67%) as an off-white solid: mp 209-211° C. IR (KBr) 3356, 1721, 776 $cm^{-1}$; $^1H$ NMR (DMSO-$d_6$, 300 MHz) δ 8.97 (s, 1H), 8.86 (d, J=4.9 Hz, 1H), 7.77 (m, 3H), 7.48 (t, J=6.1 Hz, 2H), 7.28 (t, J=7.5 Hz, 1H), 7.10 (br s, 1H), 6.69 (s, 1H).

3-(Hydroxymethyl)-N-phenylisonicotinamide (17)

Compound 16 (3.0 g, 13 mmol) was dissolved in MeOH (65 mL), $NaBH_4$ (0.902 g, 26.4 mmol) was added and the mixture was stirred at room temperature for 5 h. MeOH was evaporated under vacuum and water (28 mL) was added to the residue. This mixture was extracted with EtOAc (2×100 mL). The combined organic layer was dried over $Na_2SO_4$, concentrated and purified by silica gel flash column chromatography (70:30 EtOAc-hexanes) to afford compound 17 (2.5 g, 82%) as a light yellow syrup. IR (KBr) 3451, 1675, 666 $cm^{-1}$; $^1H$ NMR (CDCl$_3$, 300 MHz) δ 9.77 (s, 1H), 8.60 (d, J=5.1 Hz, 1H), 8.46 (s, 1H), 7.67 (m, 3H), 7.38 (t, J=7.5 Hz, 2H), 7.17 (t, J=6.6 Hz, 1H), 4.72 (s, 2H).

5-Azaphthalide (18)

Compound 17 (2.5 g, 11 mmol) was added to hydrochloric acid (15%, 22 mL), and the reaction mixture was heated at 60° C. for 2 d. The mixture was adjusted to pH 5-6 (NaHCO$_3$). The solution was extracted with CHCl$_3$ (3×75 mL). The combined organic layer was dried over Na$_2$SO$_4$, concentrated and purified by silica gel flash column chromatography (60:40 EtOAc-hexanes) to afford compound 18 (1.0 g, 68%) as a light yellow solid: mp 101-103° C. IR (KBr) 1778, 1589, 1423, 1003, 741 $cm^{-1}$; $^1H$ NMR (CDCl$_3$, 300 MHz) δ 8.94 (s, 1H), 8.85 (d, J=4.9 Hz, 1H), 7.79 (d, J=4.9 Hz, 1H), 5.43 (s, 2H); ESIMS m/z (rel intensity) 136 (MH$^+$, 100).

5-Aza-3-bromophthalide (19)

Compound 18 (1.0 g, 7.4 mmol) was combined with NBS (1.4 g, 8.1 mmol) and AIBN (20 mg) in dry CH$_2$Cl$_2$—CCl$_4$ (10:50 mL) and the mixture was heated to reflux for 48 h. The reaction mixture was cooled to room temperature, solids were filtered off, and the filtrate was concentrated and purified by silica gel flash column chromatography (50:50 EtOAc-hexanes) to afford 19 (0.750 g, 51%) as a light brown syrup. IR (film) 1784, 1587, 1422, 667 $cm^{-1}$; $^1H$ NMR (CDCl$_3$, 300 MHz) δ 9.05 (s, 1H), 8.94 (d, J=5.0 Hz, 1H), 7.82 (d, J=5.1 Hz, 1H), 7.48 (s, 1H); CIMS m/z (rel intensity) 214 (MH$^+$, 100).

5-Aza-3-hydroxyphthalide (20)

Compound 19 (0.75 g, 3.5 mmol) was heated to reflux in H$_2$O (25 mL) for 2 h before the solvent was evaporated to afford compound 20 (0.500 g, 95%) as a light yellow thick syrup: IR (film) 3215, 1726, 1622, 1078, 756 $cm^{-1}$; $^1H$ NMR (CDCl$_3$, 300 MHz) δ 9.01 (s, 1H) 8.78 (d, J=3.7 Hz, 1H), 8.22 (d, J=7.7 Hz, 1H), 6.67 (s, 1H); ESIMS m/z (rel intensity) 152 (MH$^+$, 100).

2-Azaindeno[1,2-c]isochromene-5,11-dione (21)

Following general procedure A, 21 (0.400 g, 48%) was obtained as an orange-red solid: mp 208-209° C. IR (KBr) 1755, 1702, 1490, 996, 691 $cm^{-1}$; $^1H$ NMR (CDCl$_3$, 300 MHz) δ 9.69 (s, 1H), 8.80 (d, J=5.1 Hz, 1H), 8.04 (d, J=5.1 Hz, 1H), 7.63 (dd, J=1.0, 7.4 Hz, 1H), 7.49 (m, 3H); ESIMS m/z (rel intensity) 250 (MH$^+$, 100); HRESIMS calcd for $C_{15}H_8NO_3$ 250.0504 (MH$^+$), found 250.0503.

6-Azaphthalide (23/72)

The method of Orlek and coworkers[62] was followed to yield 72 (1.5 g, 33%) as an off-white solid: mp 128-130° C. (lit.[62] mp 150-153° C.). IR (KBr) 1764, 1572, 1432, 1005, 756 $cm^{-1}$; $^1H$ NMR (CDCl$_3$, 300 MHz) δ 9.18 (s, 1H), 8.86 (d, J=5.2 Hz, 1H), 7.50 (d, J=5.2 Hz, 1H), 5.35 (s, 2H); ESIMS m/z (rel intensity) 136 (MH$^+$, 100).

6-Aza-3-bromophthalide (24)

Furo[3,4-c]pyridin-3(1H)-one (72, 1.0 g, 7.4 mmol) was heated at reflux with NBS (1.4 g, 8.1 mmol) and AIBN (20 mg) in CCl$_4$ (40 mL) for 2 h. The reaction mixture was cooled to room temperature, precipitated solids were filtered off, and the filtrate was concentrated. The residue was purified by silica gel column chromatography, eluting with 3:1 EtOAc-hexanes, to afford 24 (0.90 g, 57%) as a white solid: mp 96-97° C. IR (KBr) 1745, 1587, 668 $cm^{-1}$; $^1H$ NMR (CDCl$_3$, 300 MHz) δ 9.22 (s, 1H), 8.99 (d, J=5.2 Hz, 1H), 7.60 (d, J=5.2 Hz, 1H), 7.36 (s, 1H).

6-Aza-3-hydroxyphthalide (25)

Compound 24 (0.8 g, 4 mmol) was heated at reflux in H$_2$O (40 mL) for 2 h. The obtained mixture was concentrated to dryness to afford compound 25 (0.5 g, 88%) as a brown syrup. IR (KBr) 3256, 1734, 1081, 768 $cm^{-1}$; $^1H$ NMR (CDCl$_3$, 300 MHz) δ 10.62 (s, 0.1H), 9.16 (s, 1H), 8.98 (s, 1H), 7.87 (d, J=4.4 Hz, 1H), 6.76 (s, 0.9H); ESIMS m/z (rel intensity) 152 (MH$^+$, 100).

3-Azaindeno[1,2-c]isochromene-5,11-dione (26)

Hydroxyphthalide 25 (0.5 g, 3 mmol) and phthalide (0.413 g, 3.08 mmol) were diluted in EtOAc (15 mL). Sodium metal (0.354 g, 15.4 mmol) was dissolved in MeOH (30 mL) and the solution was added to reaction mixture. The solution was heated at reflux for 24 h, cooled to room temperature, acidified with concd HCl (~4 mL), and concentrated. The obtained solid was diluted with Ac$_2$O (20 mL) and the mixture was heated at reflux for 6 h. The solution was concentrated, diluted with CHCl$_3$ (100 mL), and washed with saturated NaHCO$_3$ (3×50 mL). The organic layer was washed with brine (75 mL), dried over Na$_2$SO$_4$, concentrated and purified by silica gel column chromatography, eluting with 9:1 CHCl$_3$-hexanes to yield 26 (0.090 g, 11%) as an orange solid: mp 203-205° C. IR (KBr) 1745, 1706, 1389, 998, 693 $cm^{-1}$; $^1H$ NMR (CDCl$_3$) δ 9.43 (s, 1H), 8.89 (d, J=5.0 Hz, 1H), 8.15 (d, J=5.2 Hz, 1H), 7.66 (m, 1H), 7.55 (m, 3H); CIMS (m/z relative intensity) 250 (MH+, 100); HRESIMS calcd for $C_{15}H_8NO_3$ 250.0504 (MH+), found 250.0495.

2-(Methoxycarbonyl)nicotinic Acid (27)

Compound 7 (5.0 g, 34 mmol) was dissolved in MeOH (25 mL). The mixture was heated to reflux for 2 h and the solvent was then removed. The resulting white solid was dissolved in EtOAc (25 mL) at reflux and filtered to remove insoluble byproducts. The filtrate was concentrated in vacuo and recrystallized from EtOAc to provide 27 (4.5 g, 71%) as a white solid: mp 157-159° C. $^1$H NMR (300 MHz, $CDCl_3$) δ 8.84 (dd, J=1.7, 5.0 Hz, 1H), 8.34 (dd, J=1.6, 7.9 Hz, 1H), 7.57 (dd, J=5.0, 8.1 Hz, 1H), 4.00 (s, 3H).

7-Azaphthalide (28)

A solution of compound 27 (4.5 g, 25 mmol) in THF (100 mL) was treated with CDI (5.35 g, 33.1 mmol) at 0° C. After 1 h, $NaBH_4$ (1.40 g, 41.2 mmol) was added in portions. The mixture was stirred for 2 h and then quenched carefully with MeOH. EtOAc (50 mL) was added. The organic layer was washed with water (75 mL) and brine (25 mL), dried over dried over anhydrous $Na_2SO_4$, and concentrated. The residue was purified by flash chromatography (80:20 EtOAc-hexanes) to give 28 (1.5 g, 45%) as a white solid: mp 142-144° C. IR (KBr) 1785, 1577, 1005, 754 $cm^{-1}$; $^1$H NMR (300 MHz, $CDCl_3$) δ 8.87 (d, J=4.6 Hz, 1H), 7.95 (d, J=8.4 Hz, 1H), 7.59 (dd, J=4.7, 7.3 Hz, 1H), 5.38 (s, 2H); ESIMS m/z (rel intensity) 136 (MH+, 100).

7-Aza-3-bromophthalide (29)

Compound 28 (1.0 g, 7.4 mmol) was heated to reflux with NBS (2.10 g, 12.1 mmol) and AIBN (30 mg) in dry $CCl_4$ (60 mL) for 24 h. The reaction mixture was cooled to room temperature, solids were filtered off, and the filtrate was concentrated and purified by silica gel flash column chromatography (60:40 hexanes-EtOAc) to afford product 29 (0.550 g 42%) as a white solid: mp 112-113° C. IR (KBr) 1782, 1590, 982, 665 $cm^{-1}$; $^1$H NMR ($CDCl_3$, 300 MHz) δ 8.96 (d, J=3.5 Hz, 1H), 8.03 (dd, J=1.3, 8.0 Hz, 1H), 7.69 (dd, J=4.8, 8.0 Hz, 1H), 7.43 (s, 1H); CIMS m/z (rel intensity) 214 (MH+, 100).

7-Aza-3-hydroxyphthalide (30)

Compound 29 (0.75 g, 3.5 mmol) was heated at reflux in $H_2O$ (25 mL) for 2 h before the solvent was evaporated to afford compound 30 (0.530 g, 99%) as a light yellow thick syrup. IR (film) 3165, 1729, 1622, 1075, 758 $cm^{-1}$; $^1$H NMR ($CDCl_3$, 300 MHz) δ 8.89 (d, J=3.7 Hz, 1H), 8.19 (d, J=7.7 Hz, 1H), 7.77 (m, 1H), 6.71 (s, 1H); ESIMS m/z (rel intensity) 152 (MH+, 100).

4-Azaindeno[1,2-c]isochromene-5,11-dione (31)

Following general procedure A, 31 (0.350 g, 42%) was obtained as an orange-red solid: mp 262-263° C. IR (KBr) 1756, 1710, 1367, 998, 636 $cm^{-1}$; $^1$H NMR ($CDCl_3$, 300 MHz) δ 8.86 (dd, J=1.5, 4.5 Hz, 1H), 8.70 (dd, J=1.5, 8.2 Hz, 1H), 7.71 (m, 1H), 7.62 (d, J=6.8 Hz, 1H), 7.52 (m, 3H); CIMS (m/z rel intensity) 250 (MH+, 100); HRESIMS calcd for $C_{15}H_8NO_3$ 250.0504 (MH+), found 250.0506.

General Procedure B.

3-Aminopropylmorpholine (32, 0.043 g, 0.301 mmol) was added to a solution of the corresponding lactone (0.050 g, 0.2 mmol) in $CHCl_3$ (30 mL). The solution was allowed to stir at reflux temperature for 15 h, diluted with $CHCl_3$ (45 mL) and washed with $H_2O$ (3×25 mL) and sat. NaCl (25 mL). The organic layer was dried over sodium sulfate, filtered, and concentrated to provide a crude solid. The solid was purified by silica gel flash column chromatography (1% MeOH in $CHCl_3$) to provide the product, 36, 37, 38, or 39.

1-Aza-5,6-dihydro-6-(3-morpholinopropyl)-5,11-dioxo-indeno[1,2-c]isoquinoline (36)

Following general procedure B, 36 (0.057 g, 85%) was obtained as an orange solid: mp 223-224° C. IR (KBr) 1702, 1658, 1494, 763 $cm^{-1}$; $^1$H NMR ($CDCl_3$, 300 MHz) δ 9.09 (dd, J=1.7, 4.5 Hz, 1H), 8.59 (dd, J=1.7, 8.0 Hz, 1H), 7.82 (m, 1H), 7.73 (m, 1H), 7.47 (m, 2H), 7.39 (m, 1H), 4.66 (t, J=7.8 Hz, 2H), 3.72 (m, 4H), 2.59 (t, J=6.3 Hz, 2H), 2.49 (m, 4H), 2.11 (m, 2H); CIMS (m/z rel intensity) 376 (MH+, 100); HRESIMS calcd for $C_{22}H_{22}N_3O_3$ 376.1662 (MH+), found 376.1667; HPLC purity, 99.39% (1% TFA in MeOH:$H_2O$, 90:10).

2-Aza-5,6-dihydro-6-(3-morpholinopropyl)-5,11-dioxo-indeno[1,2-c]isoquinoline (37)

Following general procedure B, 37 (0.066 g, 90%) was obtained as an orange-red solid: mp 218-219° C. IR (KBr) 1723, 1678, 789 $cm^{-1}$; $^1$H NMR ($CDCl_3$, 300 MHz) δ 10.0 (s, 1H), 8.68 (d, J=5.4 Hz, 1H), 8.06 (d, J=5.8 Hz, 1H), 7.78 (d, J=7.8 Hz, 1H), 7.66 (dd, J=1.3, 6.2 Hz, 1H), 7.46 (m, 2H), 4.63 (t, J=7.8 Hz, 2H), 3.72 (t, J=4.2 Hz, 4H), 2.60 (t, J=5.9 Hz, 2H), 2.50 (m, 4H), 2.08 (m, 2H); CIMS (m/z rel intensity) 376 (MH+, 100); HRESIMS calcd for $C_{22}H_{22}N_3O_3$ 376.1662 (MH+), found 376.1663; HPLC purity, 95.54% (1% TFA in MeOH:$H_2O$, 90:10).

3-Aza-5,6-dihydro-6-(3-morpholinopropyl)-5,11-dioxo-11H-indeno[1,2-c]isoquinoline (38)

3-Morpholinopropylamine (0.043 g, 0.30 mmol) was added to a solution of lactone 26 (0.050 g, 0.20 mmol) in $CHCl_3$ (30 mL). The solution was allowed to stir at reflux temperature for 15 h, diluted with $CHCl_3$ (45 mL) and washed with $H_2O$ (3×25 mL) and brine (25 mL). The organic layer was dried over sodium sulfate, filtered, and concentrated to provide a crude solid. The solid was purified by silica gel column chromatography, eluting with 1% MeOH in $CHCl_3$, to provide 38 (0.058 mg, 82%) as an orange-red solid: mp 210-211° C. IR (KBr) 1756, 1665, 1189, 756 $cm^{-1}$; $^1$H NMR ($CDCl_3$, 300 M Hz) δ 9.50 (s, 1H), 8.77 (d, J=5.5 Hz, 1H), 8.43 (d, J=5.5 Hz, 1H), 7.82 (d, J=6.1 Hz, 1H), 7.71 (d, J=6.1 Hz, 1H), 7.53 (m, 2H), 4.66 (t, J=7.6 Hz, 2H), 3.77 (br s, 4H), 2.60 (m, 6H), 2.12 (m, 2H); ESIMS (m/z relative intensity) 376 (MH+, 100); HRESIMS calcd for $C_{22}H_{22}N_3O_3$ 376.1661 (MH+), found 376.1662; HPLC purity, 95.31% (1% TFA in MeOH—$H_2O$, 90:10).

4-Aza-5,6-dihydro-6-(3-morpholinopropyl)-5,11-dioxo-indeno[1,2-c]isoquinoline (39)

Following general procedure B, 39 (0.067 g, 90%) was obtained as an orange-red solid: mp 177-178° C. IR (KBr) 1707, 1685, 1494, 765 $cm^{-1}$; $^1$H NMR ($CDCl_3$, 300 MHz)

δ 9.03 (dd, J=1.6, 8.3 Hz, 1H), 8.83 (dd, J=1.6, 4.3 Hz, 1H), 7.81 (d, J=6.5 Hz, 1H), 7.64 (m, 2H), 7.59 (m, 2H), 4.70 (t, J=7.9 Hz, 2H), 3.69 (t, J=4.6 Hz, 4 h), 2.59 (t, J=6.2 Hz, 2H), 2.48 (m, 4H), 2.09 (m, 2H); CIMS (m/z rel intensity) 376 (MH+, 100); HRESIMS calcd for $C_{22}H_{22}N_3O_3$ 376.1662 (MH+), found 376.1664; HPLC purity, 99.49% (1% TFA in MeOH:$H_2O$, 90:10).

General Procedure C.

3-Aminopropylimidazole (33, 0.037 g, 0.301 mmol) was added to a solution of the corresponding lactone (0.050 g, 0.2 mmol) in CHCl$_3$ (30 mL). The solution was allowed to stir at reflux temperature for 15 h, diluted with CHCl$_3$ (50 mL) and washed with H$_2$O (3×20 mL) and sat. NaCl (20 mL). The organic layer was dried over Na$_2$SO$_4$, filtered, and concentrated to provide a crude solid. The solid was purified by silica gel flash column chromatography (3% MeOH in CHCl$_3$) to provide the product, 40, 41, 42, or 43.

1-Aza-5,6-dihydro-6-(3-(1H-imidazol-1-yl)propyl)-5,11-dioxo-indeno[1,2-c]isoquinoline (40)

Following general procedure C, 40 (0.052 g, 82%) was obtained as an orange-red solid: mp 242-243° C. IR (KBr) 1702, 1667, 1495, 761, 665 cm$^{-1}$; $^1$H NMR (CDCl$_3$, 300 MHz) δ 9.09 (dd, J=1.9, 4.5 Hz, 1H), 8.58 (dd, J=1.9, 8.2 Hz, 1H), 7.71 (d, J=7.0 Hz, 1H), 7.64 (s, 1H), 7.43 (m, 3H), 7.19 (s, 1H), 7.07 (s, 1H), 6.75 (d, J=7.5 Hz, 1H), 4.58 (t, J=7.4 Hz, 2H), 4.27 (t, J=6.2 Hz, 2H), 2.43 (m, 2H); ESIMS (m/z rel intensity) 357 (MH+, 100); HRESIMS calcd for $C_{21}H_{17}N_4O_2$ 357.1352 (MH+), found 357.1359; HPLC purity, 98.36% (1% TFA in MeOH:H$_2$O, 90:10).

2-Aza-5,6-dihydro-6-(3-(1H-imidazol-1-yl)propyl)-5,11-dioxo-indeno[1,2-c]isoquinoline (41)

Following general procedure C, 41 (0.063 g, 87%) was obtained as an orange-red solid: mp 274-275° C. IR (KBr) 1708, 1689, 768, 656 cm$^{-1}$; $^1$H NMR (CDCl$_3$+CD$_3$OD, 300 MHz) δ 9.86 (s, 1H), 8.56 (d, J=5.5 Hz, 1H), 8.02 (d, J=5.5 Hz, 1H), 7.69 (s, 1H), 7.57 (dd, J=1.2, 6.8 Hz, 1H), 7.36 (m, 2H), 7.06 (d, J=4.2 Hz, 1H), 6.81 (d, J=7.3 Hz, 1H), 4.49 (t, J=7.5 Hz, 2H), 4.21 (t, J=6.5 Hz, 2H), 2.33 (m, 2H); ESIMS (m/z rel intensity) 357 (MH+, 100); HRESIMS calcd for $C_{21}H_{17}N_4O_2$ 357.1352 (MH+), found 357.1354; HPLC purity, 96.57% (1% TFA in MeOH:H$_2$O, 90:10).

3-Aza-5,6-dihydro-6-(3-(1H-imidazol-1-yl)propyl)-5,11-dioxo-11H-indeno[1,2-c]isoquinoline (42)

1-(3-Aminopropyl)imidazole (0.037 g, 0.30 mmol) was added to a solution of lactone 26 (0.050 g, 0.20 mmol) in CHCl$_3$ (30 mL). The solution was allowed to stir at reflux temperature for 15 h, diluted with CHCl$_3$ (50 mL) and washed with H$_2$O (3×20 mL) and brine (20 mL). The organic layer was dried over sodium sulfate, filtered, and concentrated to provide a crude solid. The solid was purified by silica gel column chromatography, eluting with 97:3 CHCl$_3$-MeOH, to provide 42 (0.030 mg, 71%) as an orange-red solid: mp 251-252° C. IR (KBr) 1723, 1678, 767, 685 cm$^{-1}$; $^1$H NMR (CDCl$_3$, 300 MHz) δ 9.52 (s, 1H), 8.79 (d, J=5.6 Hz, 1H), 8.42 (d, J=5.5 Hz, 1H), 7.68 (m, 2H), 7.46 (t, J=7.0 Hz, 1H), 7.36 (t, J=7.0 Hz, 1H), 7.21 (s, 1H), 7.07 (s, 1H), 6.71 (d, J=7.4 Hz, 1H), 4.56 (t, J=7.8 Hz, 2H), 4.28 (t, J=6.2 Hz, 2H), 2.37 (m, 2H); ESIMS (m/z relative intensity) 357 (MH+, 100); HRESIMS calcd for $C_{21}H_{17}N_4O_2$ 357.1352 (MH+), found 357.1351; HPLC purity, 95.74% (1% TFA in MeOH—H$_2$O, 90:10).

4-Aza-5,6-dihydro-6-(3-(1H-imidazol-1-yl)propyl)-5,11-dioxo-indeno[1,2-c]isoquinoline (43)

Following general procedure C, 43 (0.061 g, 86%) was obtained as an orange-red solid: mp 251-252° C. IR (KBr) 1712, 1687, 778, 666 cm$^{-1}$; $^1$H NMR (CDCl$_3$, 300 MHz) δ 9.00 (dd, J=1.6, 8.3 Hz, 1H), 8.84 (dd, J=1.7, 4.4 Hz, 1H), 7.64 (s, 1H), 7.62 (m, 2H), 7.58 (m, 2H), 7.18 (s, 1H), 7.07 (s, 1H), 6.66 (d, J=7.3 Hz, 1H), 4.60 (t, J=7.5 Hz, 2H), 4.28 (t, J=6.2 Hz, 2H), 2.28 (m, 2H); ESIMS (m/z rel intensity) 357 (MH+, 100); HRESIMS calcd for $C_{21}H_{17}N_4O_2$ 357.1352 (MH+), found 357.1358; HPLC purity, 99.80% (1% TFA in MeOH:H$_2$O, 90:10).

General Procedure D.

N,N-Dimethylaminopropylamine (34, 0.030 g, 0.301 mmol) was added to a solution of corresponding lactone (0.050 g, 0.2 mmol) in CHCl$_3$ (30 mL). The solution was allowed to stir at reflux temperature for 15 h, diluted with CHCl$_3$ (60 mL) and washed with H$_2$O (3×30 mL) and brine (30 mL). The organic layer was dried over Na$_2$SO$_4$, filtered, and concentrated to provide a crude solid. The solid was purified by silica gel flash column chromatography (4% MeOH in CHCl$_3$) to afford the product, 44, 45, 46, or 47.

1-Aza-5,6-dihydro-6-(3-(dimethylamino)propyl)-5,11-dioxo-indeno[1,2-c]isoquinoline (44)

Following general procedure D, 44 (0.055 g, 84%) was obtained as an orange-red solid: mp 187-188° C. IR (KBr) 1704, 1659, 1554, 764 cm$^{-1}$; $^1$H NMR (CDCl$_3$, 300 MHz) δ 9.09 (dd, J=1.8, 4.6 Hz, 1H), 8.61 (dd, J=1.8, 8.0 Hz, 1H), 7.88 (m, 1H), 7.85 (m, 1H), 7.49 (m, 2H), 7.46 (m, 1H), 4.64 (m, 2H), 2.52 (t, J=6.5 Hz, 2H), 2.29 (s, 6H), 2.06 (m, 2H); CIMS (m/z rel intensity) 334 (MH+, 100); HRESIMS calcd for $C_{20}H_{20}N_3O_2$ 334.1556 (MH+), found 334.1562; HPLC purity, 98.32% (1% TFA in MeOH:H$_2$O, 90:10).

2-Aza-5,6-dihydro-6-(3-(dimethylamino)propyl)-5,11-dioxo-indeno[1,2-c]isoquinoline (45)

Following general procedure D, 45 (0.059 g, 86%) was obtained as an orange-red solid: mp 177-178° C. IR (KBr) 1709, 1667, 1492, 768 cm$^{-1}$; $^1$H NMR (CDCl$_3$, 300 MHz) δ 10.0 (s, 1H), 8.68 (d, J=5.2 Hz, 1H), 8.07 (d, J=5.3 Hz, 1H), 7.81 (d, J=7.2 Hz, 1H), 7.66 (d, J=7.0 Hz, 1H), 7.47 (m, 2H), 4.61 (m, 2H), 2.54 (t, J=6.5 Hz, 2H), 2.06 (m, 2H); CIMS (m/z rel intensity) 334 (MH+, 100); HRESIMS calcd for $C_{20}H_{20}N_3O_2$ 334.1556 (MH+), found 334.1560; HPLC purity, 98.21% (1% TFA in MeOH:H$_2$O, 90:10).

3-Aza-5,6-dihydro-6-(3-(dimethylamino)propyl)-5,11-dioxo-11H-indeno[1,2-c]isoquinoline (46)

N,N-Dimethyl-1,3-diaminopropane (0.030 g, 0.30 mmol) was added to a solution of lactone 26 (0.050 g, 0.20 mmol) in CHCl$_3$ (30 mL). The solution was allowed to stir at reflux temperature for 15 h, diluted with CHCl$_3$ (60 mL) and washed with H$_2$O (3×30 mL) and brine (30 mL). The organic layer was dried over sodium sulfate, filtered, and concentrated to provide a crude solid. The solid was purified by silica gel column chromatography, eluting with 4% MeOH in CHCl$_3$, to afford 46 (0.049 g, 72%) as an orange-red solid: mp 168-170° C. IR (KBr) 1710, 1675, 1567, 765 cm$^{-1}$; $^1$H NMR (CDCl$_3$, 300 M Hz) δ 9.50 (s, 1H), 8.75 (dd, J=5.5 Hz, 1H), 8.40 (d, J=5.7 Hz, 1H), 7.79 (m, 1H), 7.68 (m, 1H), 7.50 (m, 2H), 4.61 (m, 2H), 2.53 (t, J=6.45 Hz, 2H), 2.29 (s, 6H), 2.05 (m, 2H); CIMS (m/z relative intensity) 334 (MH$^+$, 100); HRESIMS calcd for $C_{20}H_{20}N_3O_2$ 334.1556 (MH$^+$), found 334.1557; HPLC purity, 99.46% (1% TFA in MeOH—H$_2$O, 90:10).

4-Aza-5,6-dihydro-6-(3-(dimethylamino)propyl)-5,11-dioxo-indeno[1,2-c]isoquinoline (47)

Following general procedure D, 47 (0.056 g, 84%) was obtained as an orange-red solid: mp 183-184° C. IR (KBr) 1712, 1678, 1489, 767 cm$^{-1}$; $^1$H NMR (CDCl$_3$, 300 MHz) δ 9.03 (dd, J=1.5 Hz, 8.2 Hz, 1H), 8.82 (dd, J=2.7, 4.2 Hz, 1H), 7.86 (d, J=7.1 Hz, 1H), 7.62 (m, 2H), 7.58 (m, 2H), 4.67 (m, 2H), 2.53 (t, J=6.5 Hz, 2H), 2.28 (s, 6H), 2.07 (m, 2H); CIMS (m/z rel intensity) 334 (MH$^+$, 100); HRESIMS calcd for $C_{20}H_{20}N_3O_2$ 334.1556 (MH$^+$), found 334.1559; HPLC purity, 99.62% (1% TFA in MeOH:H$_2$O, 90:10).

(2'S)-1-Aza-5,6-dihydro-6-(2',3'-dihydroxypropyl)-5,11-dioxo-indeno[1,2-c]isoquinoline (48)

Lactone 13 (54 mg, 0.22 mmol) was suspended with stirring in CHCl$_3$ (10 mL) and MeOH (2.5 mL). Amine 35 (32 mg, 0.35 mmol) dissolved in MeOH (0.5 mL) was added to the suspension and it was stirred with heating to reflux for 17.5 h. The mixture was cooled to room temperature and concentrated in vacuo. H$_2$O (5 mL) was added and the suspension was filtered to collect the solid. Compound 48 (27 mg, 39%) was obtained as a red-orange solid: mp 245-250° C. (dec). $^1$H NMR (300 MHz, DMSO-d$_6$) δ 9.00 (dd, J=4.5, 1.9 Hz, 1H), 8.50 (dd, J=8.1, 1.9 Hz, 1H), 8.14 (d, J=7.3 Hz, 1H), 7.67-7.42 (m, 4H), 5.15 (d, J=5.0 Hz, 1H), 5.00 (t, J=5.6 Hz, 1H), 4.58 (d, J=6.7 Hz, 2H), 4.10-3.90 (m, 1H), 3.60 (t, J=5.4 Hz, 2H); ESIMS m/z (rel intensity) 345 (MNa$^+$, 100); HRESIMS m/z calcd for $C_{18}H_{14}N_2O_4Na$ 345.0852 (MNa$^+$), found 345.0861; HPLC purity, 100% (MeOH, 100).

(2'S)-2-Aza-5,6-dihydro-6-(2',3'-dihydroxypropyl)-5,11-dioxo-indeno[1,2-c]isoquinoline (49)

Lactone 21 (50 mg, 0.20 mmol) was suspended with stirring in CHCl$_3$ (10 mL) and MeOH (2.5 mL). Amine 35 (26 mg, 0.29 mmol) dissolved in MeOH (0.5 mL) was added to the suspension and it was stirred with heating to reflux for 23 h. The mixture was cooled to room temperature and concentrated in vacuo. H$_2$O (1 mL) was added and the suspension was filtered to provide a collect solid. Compound 49 (27 mg, 42%) was obtained as a red-orange solid: mp 229-232° C. $^1$H NMR (300 MHz, DMSO-d$_6$) δ 9.82 (d, J=1.0 Hz, 1H), 8.66 (d, J=5.3 Hz, 1H), 8.07 (d, J=7.4 Hz, 1H), 8.01 (dd, J=5.4, 1.0 Hz, 1H), 7.61-7.46 (m, 3H), 5.14 (d, J=5.0 Hz, 1H), 5.01 (t, J=5.6 Hz, 1H), 4.60-4.46 (m, 2H), 4.05-3.92 (m, 1H), 3.65-3.53 (m, 2H); CIMS m/z (rel intensity) 323 (MH$^+$, 100); HRESIMS m/z calcd for $C_{18}H_{15}N_2O_4$ 323.1032 (MH$^+$), found 323.1045; HPLC purity, 100% (MeOH, 100).

(2'S)-3-Aza-5,6-dihydro-6-(2',3'-dihydroxypropyl)-5,11-dioxo-indeno[1,2-c]isoquinoline (50)

Lactone 26 (11 mg, 0.044 mmol) was suspended with stirring in CHCl$_3$ (1 mL) and a solution of the amine 35 (7 mg, 0.08 mmol) in MeOH (1 mL) was added. The mixture was stirred at room temperature for 1 h and concentrated in vacuo. The residue was purified by silica gel column chromatography, eluting with 95:5 CHCl$_3$-MeOH, to yield 50 (6 mg, 42%) as a yellow-orange solid: mp 237-238° C. $^1$H NMR (300 MHz, DMSO-d$_6$) δ 9.32 (s, 1H), 8.79 (d, J=5.5 Hz, 1H), 8.32 (dd, J=5.5, 0.9 Hz, 1H), 8.17 (d, J=7.3 Hz, 1H), 7.68-7.48 (m, 3H), 5.17 (d, J=5.0 Hz, 1H), 5.02 (t, J=5.6 Hz, 1H), 4.65-4.46 (m, 2H), 4.07-3.93 (m, 1H), 3.60 (t, J=5.3 Hz, 2H); ESIMS m/z (rel intensity) 323 (MH$^+$, 100); HRESIMS m/z calcd for $C_{18}H_{15}N_2O_4$ 323.1032 (MH$^+$), found 323.1024; HPLC purity, 100% (MeOH, 100).

(2'S)-4-Aza-5,6-dihydro-6-(2',3'-dihydroxypropyl)-5,11-dioxo-indeno[1,2-c]isoquinoline (51)

Lactone 31 (46 mg, 0.18 mmol) was suspended with stirring in CHCl$_3$ (10 mL) and MeOH (2.5 mL). A solution of the amine 35 (21 mg, 0.23 mmol) in MeOH (0.5 mL) was added to the suspension and the mixture was stirred at room temperature for 2 h and with heating to reflux for 23 h. The mixture was cooled to room temperature and concentrated in vacuo. H$_2$O (1 mL) was added and the suspension was filtered to yield a solid. Compound 51 (27 mg, 45%) was obtained as a yellow-orange solid: mp 247-255° C. $^1$H NMR (300 MHz, DMSO-d$_6$) δ 8.90 (dd, J=8.3, 1.7 Hz, 1H), 8.78 (dd, J=4.3, 1.7 Hz, 1H), 8.09 (d, J=7.5 Hz, 1H), 7.77 (dd, J=8.3, 4.3 Hz, 1H), 7.62-7.41 (m, 3H), 5.14 (d, J=5.0 Hz, 1H), 5.00 (t, J=5.6 Hz, 1H), 4.65-4.43 (m, 2H), 4.09-3.94 (m, 1H), 3.60 (t, J=5.3 Hz, 2H); ESIMS m/z (rel intensity) 323 (MH$^+$, 100); HRESIMS m/z calcd for $C_{18}H_{15}N_2O_4$ 323.1032 (MH$^+$), found 323.1038; HPLC purity, 100% (MeOH, 100).

General Procedure E.

A solution of N-Boc-1,3-diaminopropane (52, 0.068 g, 0.4 mmol) in CHCl$_3$ (10 mL) was added to the appropriate lactone (0.050 g, 0.2 mmol) in CHCl$_3$ (25 mL). The reaction mixture was heated at reflux for 24 h. After completion of the reaction, CHCl$_3$ was removed under reduced pressure. The crude product was purified by silica gel flash column chromatography (95:5 CHCl$_3$-MeOH) to afford Boc-protected compounds 53-56.

1-Aza-6-(N-Boc-3-aminopropyl)-5,6-dihydro-5,11-dioxo-indeno[1,2-c]isoquinoline (53)

Following general procedure E, 53 (0.075 g, 92%) was obtained as an orange solid: mp 202-203° C. IR (KBr) 1711, 1698, 1676, 665 cm$^{-1}$; $^1$H NMR (CDCl$_3$, 300 MHz) δ 9.13 (dd, J=1.7, 4.5 Hz, 1H), 8.62 (dd, J=1.7, 8.1 Hz, 1H), 7.75 (d, J=8.1 Hz, 1H), 7.63 (d, J=8.0 Hz, 1H), 7.50 (m, 2H), 7.41 (m, 1H), 4.66 (t, J=7.0 Hz, 2H), 3.29 (m, 2H), 2.13 (m, 2H), 1.45 (s, 9H); CIMS (m/z rel intensity) 406 (MH$^+$, 100).

2-Aza-6-(N-Boc-3-aminopropyl)-5,6-dihydro-5,11-dioxo-indeno[1,2-c]isoquinoline (54)

Following general procedure E, 54 (0.072 g, 90%) was obtained as an orange-red solid: mp 184-185° C. IR (KBr) 1715, 1685, 1675, 666 cm$^{-1}$; $^1$H NMR (CDCl$_3$, 300 MHz) δ 10.0 (s, 1H), 8.70 (d, J=5.4 Hz, 1H), 8.10 (d, J=5.4 Hz, 1H), 7.69 (d, J=6.5 Hz, 1H), 7.59 (d, J=6.8 Hz, 1H), 7.49 (m, 2H), 4.63 (t, J=7.0 Hz, 2H), 3.29 (m, 2H), 2.12 (m, 2H), 1.45 (s, 9H); CIMS (m/z rel intensity) 406 (MH$^+$, 100).

3-Aza-6-(N-Boc-3-aminopropyl)-5,6-dihydro-5,11-dioxo-indeno[1,2-c]isoquinoline (55)

Following general procedure E, 55 (0.070 g, 86%) was obtained as an orange-red solid: mp 176-177° C. IR (KBr)

1708, 1694, 1671, 665 cm$^{-1}$; $^1$H NMR (CDCl$_3$, 300 MHz) δ 9.50 (s, 1H), 8.75 (d, J=5.5 Hz, 1H), 8.40 (d, J=5.6 Hz, 1H), 7.89 (m, 1H), 7.68 (m, 1H), 7.50 (m, 2H), 4.61 (m, 2H), 2.53 (t, J=6.4 Hz, 2H), 2.10 (m, 2H), 1.46 (s, 9H); CIMS (m/z rel intensity) 406 (MH$^+$, 100).

4-Aza-6-(N-Boc-3-aminopropyl)-5,6-dihydro-5,11-dioxo-indeno[1,2-c]isoquinoline (56)

Following general procedure E, 56 (0.077 g, 95%) was obtained as an orange solid: mp 197-198° C. IR (KBr) 1721, 1659, 1634, 656 cm$^{-1}$; $^1$H NMR (CDCl$_3$, 300 MHz) δ 9.06 (d, J=8.3 Hz, 1H), 8.86 (dd, J=1.5 Hz, 4.3 Hz, 1H), 7.66 (m, 3H), 7.58 (m, 2H), 4.69 (t, J=6.6 Hz, 2H), 3.26 (m, 2H), 2.12 (m, 2H), 1.43 (s, 9H); CIMS (m/z rel intensity) 406 (MH$^+$, 100).

General Procedure F.

Appropriate Boc-protected azaindenoisoquinolines 53-56 (0.065 g, 0.160 mmol) in CHCl$_3$ (20 mL) were treated with 5 N HCl in MeOH (4 mL). The reaction mixture was stirred at room temperature for 6 h. After completion of the reaction, the solvents were removed under reduced pressure and the crude product was washed with 10% MeOH in CHCl$_3$ (20 mL) and filtered to afford the dihydrochloride salts.

6-(3-Aminopropyl)-1-aza-5,6-dihydro-5,11-dioxo-indeno[1,2-c]isoquinoline Dihydrochloride (57)

Following general procedure F, 57 (0.053 g, 88%) was obtained as an orange-red solid: mp 226-228° C. IR (KBr) 3370, 1696, 1676, 763, 666 cm$^{-1}$; $^1$H NMR (DMSO-d$_6$, 300 MHz) δ 9.01 (d, J=4.3 Hz, 1H), 8.57 (d, J=8.0 Hz, 1H), 8.04 (br s, 3H), 7.91 (d, J=7.7 Hz, 1H), 7.64 (m, 4H), 4.60 (t, J=7.0 Hz, 2H), 2.99 (m, 2H), 2.16 (m, 2H); ESIMS (m/z rel intensity) 306 (MH$^+$, 100); HRESIMS calcd for C$_{18}$H$_{16}$N$_3$O$_2$ 306.1243 (MH$^+$), found 306.1247; HPLC purity, 96.16% (1% TFA in MeOH:H$_2$O, 90:10).

6-(3-Aminopropyl)-2-aza-5,6-dihydro-5,11-dioxo-indeno[1,2-c]isoquinoline Dihydrochloride (58)

Following general procedure F, 58 (0.052 g, 86%) was obtained as an orange-red solid: mp 272-274° C. IR (KBr) 3376, 1698, 1685, 765, 665 cm$^{-1}$; $^1$H NMR (DMSO-d$_6$, 300 MHz) δ 9.78 (s, 1H), 8.69 (d, J=5.4 Hz, 1H), 8.08 (d, J=5.3 Hz, 1H), 7.86 (d, J=7.8 Hz, 1H), 7.64 (m, 3H), 4.93 (br s, 3H), 4.56 (t, J=7.1 Hz, 2H), 2.99 (m, 2H), 2.15 (m, 2H); ESIMS (m/z rel intensity) 306 (MH$^+$, 100); HRESIMS calcd for C$_{18}$H$_{16}$N$_3$O$_2$ 306.1243 (MH$^+$), found 306.1249; HPLC purity, 99.62% (1% TFA in MeOH:H$_2$O, 90:10).

6-(3-Aminopropyl)-3-aza-5,6-dihydro-5,11-dioxo-indeno[1,2-c]isoquinoline Dihydrochloride (59)

Following general procedure F, 59 (0.054 g, 89%) was obtained as an orange-red solid: mp 253-254° C. IR (KBr) 3410, 1702, 1695, 784, 655 cm$^{-1}$; $^1$H NMR (DMSO-d$_6$, 300 MHz) δ 9.88 (s, 1H), 8.78 (d, J=5.6 Hz, 1H), 8.18 (d, J=5.5 Hz, 1H), 7.94 (d, J=8.0 Hz, 1H), 7.74 (m, 3H), 5.03 (br s, 3H), 4.68 (t, J=7.5 Hz, 2H), 3.05 (m, 2H), 2.10 (m, 2H); ESIMS (m/z rel intensity) 306 (MH$^+$, 100); HRESIMS calcd for C$_{18}$H$_{16}$N$_3$O$_2$ 306.1243 (MH$^+$), found 306.1244; HPLC purity, 96.81% (1% TFA in MeOH:H$_2$O, 90:10).

6-(3-Aminopropyl)-4-aza-5,6-dihydro-5,11-dioxo-indeno[1,2-c]isoquinoline Dihydrochloride (60)

Following general procedure F, 60 (0.050 g, 83%) was obtained as an orange solid: mp 284-286° C. IR (KBr) 3395, 1710, 1698, 765, 666 cm$^{-1}$; $^1$H NMR (D$_2$O, 300 MHz) δ 8.31 (s, 1H), 8.13 (br s, 1H), 7.28 (m, 3H), 7.10 (br s, 1H), 6.87 (br s, 1H), 4.20 (t, J=6.8 Hz, 2H), 3.13 (t, J=6.8 Hz, 2H), 2.12 (m, 2H); ESIMS (m/z rel intensity) 306 (MH$^+$, 100); HRESIMS calcd for C$_{18}$H$_{16}$N$_3$O$_2$ 306.1243 (MH$^+$), found 306.1245; HPLC purity, 98.75% (1% TFA in MeOH:H$_2$O, 80:20).

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

What is claimed is:

1. A compound having the formula (I)

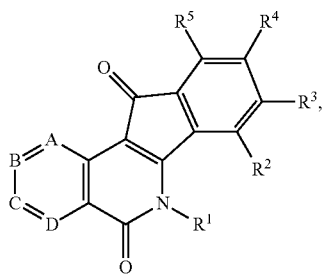

(I)

or a pharmaceutically acceptable salt, hydrate, or solvate thereof, wherein $R^1$ is an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted with one or more substituents independently selected in each instance from the group consisting of halogen, hydroxyl, alkoxy, aryloxy, aralkyloxy, oxo(carbonyl), carboxylic acid, carboxylate, carboxylate ester, thiol, alkyl sulfide, aryl sulfide, sulfoxide, sulfonyl, sulfonamide, amine, azide, hydroxylamine, cyano, nitro, hydrazide, and enamine;

$R^2$, $R^3$, $R^4$ and $R^5$ represent four substituents each independently selected in each instance from the group consisting of hydrogen, halo, azido, cyano, nitro, hydroxy, amino, thio, and derivatives thereof; or any two adjacent substituents that are taken together with the attached carbons to form a heterocycle optionally substituted with one or more substituents independently selected in each instance from the group consisting of halogen, hydroxyl, alkoxy, aryloxy, aralkyloxy, oxo(carbonyl), carboxylic acid, carboxylate, carboxylate ester, thiol, alkyl sulfide, aryl sulfide, sulfoxide, sulfonyl, sulfonamide, amine, azide, hydroxylamine, cyano, nitro, hydrazide, and enamine, and each of the other two substituents is defined as above;

A is N or CH;
B is N or CH;
C is N or CH;
D is N or CH; and
one of A, B, C, or D is N.

2. The compound according to claim 1, wherein $R^1$ is a $C_1$-$C_{12}$ alkyl, alkenyl, heteroalkyl, heteroalkenyl, or heterocyclyl optionally substituted with one or more substituents independently selected in each instance from the group consisting of halogen, hydroxyl, alkoxy, aryloxy, aralkyloxy, oxo(carbonyl), carboxylic acid, carboxylate, carboxylate ester, thiol, alkyl sulfide, aryl sulfide, sulfoxide, sulfonyl, sulfonamide, amine, azide, hydroxylamine, cyano, nitro, hydrazide, and enamine.

3. The compound according to claim 2, wherein $R^1$ is $-(CH_2)_n R$ wherein n is 2, 3 or 4 wherein R is 1-imidazolyl, and $R^2$, $R^3$, $R^4$ and $R^5$ are hydrogen.

4. The compound according to claim 2, wherein $R^1$ is $-(CH_2)_n R$ wherein n is 2, 3 or 4 and R is 1,2,4-triazol-2-yl, and $R^2$, $R^3$, $R^4$ and $R^5$ are hydrogen.

5. The compound according to claim 2, wherein $R^1$ is $-(CH_2)_n R$ wherein n is 2, 3 or 4 and R is 1-morpholinyl, and $R^2$, $R^3$, $R^4$ and $R^5$ are hydrogen.

6. The compound according to claim 2, wherein $R^1$ is $-(CH_2)_n R$ wherein n is 2, 3 or 4 and R is $N(CH_3)_2$, and $R^2$, $R^3$, $R^4$ and $R^5$ are hydrogen.

7. The compound according to claim 2, wherein $R^1$ is —$(CH_2)_nR$ wherein n is 2, 3 or 4 and R is amino, and $R^2$, $R^3$, $R^4$ and $R^5$ are hydrogen.

8. The compound according to claim 2, wherein $R^1$ is —$CH_2CH(OH)CH_2OH$, and $R^2$, $R^3$, $R^4$ and $R^5$ are hydrogen.

9. The compound according to claim 1, wherein A is N and B, C, and D are CH, and $R^2$, $R^3$, $R^4$ and $R^5$ are hydrogen.

10. The compound according to claim 1, wherein B is N and A, C, and D are CH, and $R^2$, $R^3$, $R^4$ and $R^5$ are hydrogen.

11. The compound according to claim 1, wherein C is N and A, B, and D are CH, and $R^2$, $R^3$, $R^4$ and $R^5$ are hydrogen.

12. The compound according to claim 1, wherein D is N, A, B, and C are CH, and $R^2$, $R^3$, $R^4$ and $R^5$ are hydrogen.

13. The compound according to claim 1, wherein and $R^2$, $R^3$, $R^4$ and $R^5$ are hydrogen.

14. The compound according to claim 1, wherein $R^2$ and $R^5$ are hydrogen, and $R^3$ and $R^4$ are methoxy or together with the attached carbons form a five-membered heterocycle.

15. The compound according to claim 1, wherein the compound is selected from the group consisting of

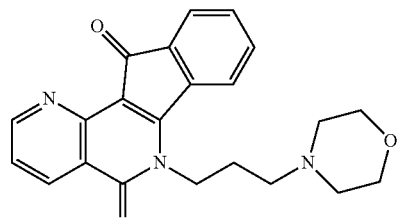

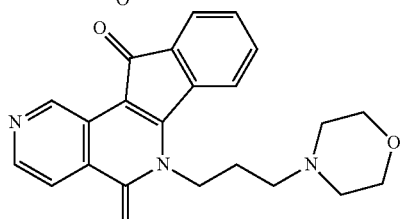

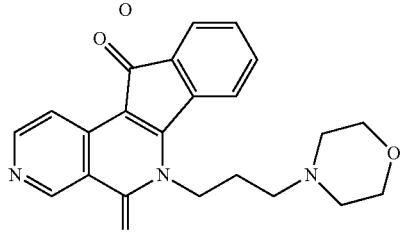

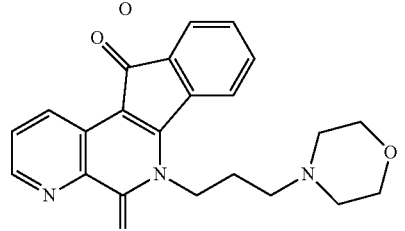

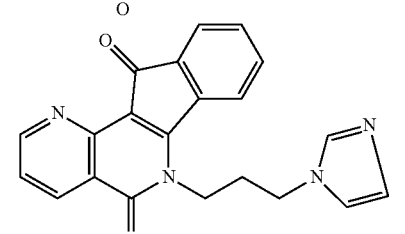

-continued

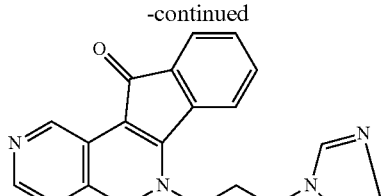

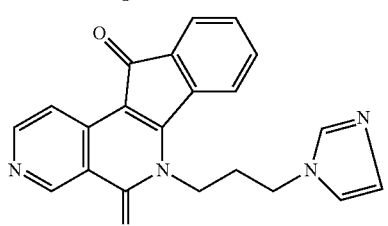

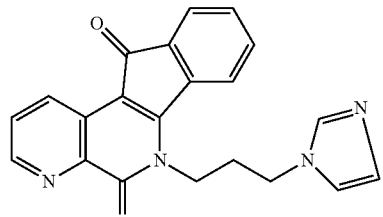

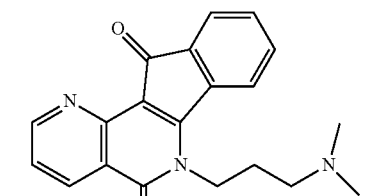

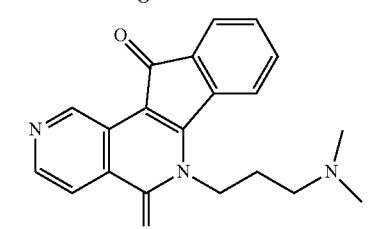

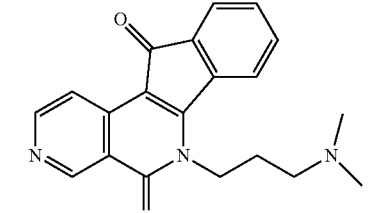

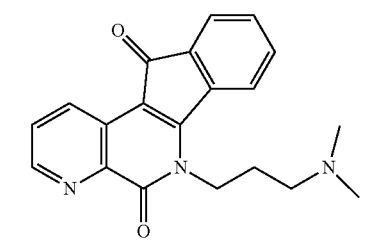

-continued

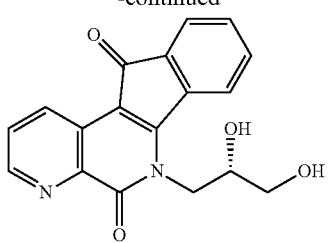

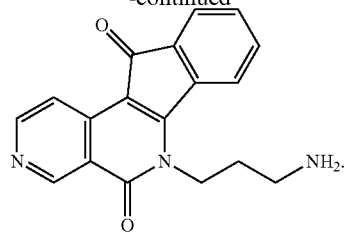

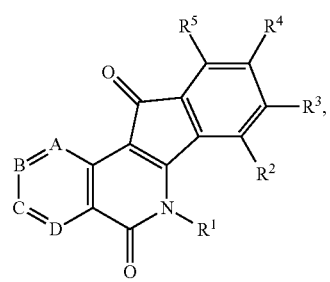
and

16. A pharmaceutical composition comprising one or more compounds of claim 1, or a pharmaceutically acceptable salt thereof, together with one or more diluents, excipients or carriers.

17. A method for treating cancer comprising the step of administering a therapeutically effective amount of one or more compounds of claim 1, and one or more carriers, diluents, or excipients, to a patient in need of relief from said cancer.

18. A method for treating cancer comprising the step of administering a therapeutically effective amount of a compound of claim 1 in combination with one or more other compounds of the same or different mode of action, and one or more carriers, diluents, or excipients, to a patient in need of relief from said cancer.

19. A method for treating cancer comprising the step of administering a therapeutically effective amount of one or more compounds of formula (I) or a pharmaceutically acceptable salt thereof, together with one or more carriers, diluents, or excipients, to a patient in need of relief from said cancer:

(I)

wherein
$R^1$ is an alkyl, alkenyl, heteroalkyl, heteroalkenyl, heterocyclyl, cycloalkyl, cycloalkenyl, cycloheteroalkyl, cycloheteroalkenyl, aryl, arylalkyl, and arylalkenyl, each of which is optionally substituted with one or more substituents independently selected in each instance from the group consisting of halogen, hydroxyl, alkoxy, aryloxy, aralkyloxy, oxo(carbonyl), carboxylic acid, carboxylate, carboxylate ester, thiol, alkyl sulfide, aryl sulfide, sulfoxide, sulfonyl, sulfonamide, amine, azide, hydroxylamine, cyano, nitro, hydrazide, and enamine;
$R^2$, $R^3$, $R^4$ and $R^5$ represent four substituents each independently selected in each instance from the group consisting of hydrogen, halo, azido, cyano, nitro, hydroxy, amino, thio, and derivatives thereof; or any two adjacent substituents that are taken together with the attached carbons to form an optionally substituted heterocycle optionally substituted with one or more substituents independently selected in each in each instance from the group consisting of halogen, hydroxyl, alkoxy, aryloxy, aralkyloxy, oxo(carbonyl), carboxylic acid, carboxylate, carboxylate ester, thiol, alkyl sulfide, aryl sulfide, sulfoxide, sulfonyl, sulfonamide, amine, azide, hydroxylamine, cyano, nitro, hydrazide, and enamine, and each of the other two substituents is defined as above;

A is N or CH;
B is N or CH;
C is N or CH;
D is N or CH; and
one of A, B, C, or D is N.

20. The method of claim 19, wherein $R^1$ is a $C_1$-$C_{12}$ alkyl, alkenyl, heteroalkyl, heteroalkenyl, or heterocyclyl optionally substituted with one or more substituents independently selected in each instance from the group consisting of halogen, hydroxyl, alkoxy, aryloxy, aralkyloxy, oxo(carbonyl), carboxylic acid, carboxylate, carboxylate ester, thiol, alkyl sulfide, aryl sulfide, sulfoxide, sulfonyl, sulfonamide, amine, azide, hydroxylamine, cyano, nitro, hydrazide, and enamine.

\* \* \* \* \*

SEQUENCE LISTING

```
<160> NUMBER OF SEQ ID NOS: 4

<210> SEQ ID NO 1
<211> LENGTH: 14
<212> TYPE: DNA
<213> ORGANISM: artificial sequence
<220> FEATURE:
<223> OTHER INFORMATION: N14Y, a 5'-end labeled DNA oligonucleotide with
      a 3'-end phosphate Tyr

<400> SEQUENCE: 1
gatctaaaag actt                                                        14

<210> SEQ ID NO 2
```

```
<211> LENGTH: 14
<212> TYPE: DNA
<213> ORGANISM: artificial sequence
<220> FEATURE:
<223> OTHER INFORMATION: N14P, 5'-end labeled DNA oligonucleaotide

<400> SEQUENCE: 2
gatctaaaag actt                                                    14

<210> SEQ ID NO 3
<211> LENGTH: 19
<212> TYPE: DNA
<213> ORGANISM: artificial sequence
<220> FEATURE:
<223> OTHER INFORMATION: Y19, a 3'-end labeled DNA-oligonucleotide, DNA
      topoisomerase IB substrate

<400> SEQUENCE: 3
atttcgtccg aagttgcct                                               19

<210> SEQ ID NO 4
<211> LENGTH: 19
<212> TYPE: DNA
<213> ORGANISM: artificial sequence
<220> FEATURE:
<223> OTHER INFORMATION: P19, a DNA oligonucleotide, topoisomerase IB
      product of Y19

<400> SEQUENCE: 4
atttcgtccg aagttgcct                                               19
```